United States Patent [19]

Holt et al.

[11] Patent Number: 5,017,568

[45] Date of Patent: May 21, 1991

[54] STERIOD 5-ALPHA-REDUCTASE INHIBITORS

[75] Inventors: Dennis A. Holt, Mohnton; Conrad J. Kowalski, Paoli; Mark A. Levy, Wayne; Brian W. Metcalf, Radnor; Ann M. Tickner, Philadelphia, all of Pa.

[73] Assignee: SmithKline Beecham Corporation, Philadelphia, Pa.

[21] Appl. No.: 499,244

[22] Filed: Mar. 23, 1990

Related U.S. Application Data

[63] Continuation-in-part of Ser. No. 182,828, Apr. 18, 1988, abandoned, which is a continuation-in-part of Ser. No. 127,147, Dec. 1, 1987, Pat. No. 4,910,226, which is a continuation-in-part of Ser. No. 43,773, Apr. 29, 1987, abandoned.

[51] Int. Cl.$^5$ .............. A61K 31/58; A61K 31/56; C07J 71/00; C07J 17/00
[52] U.S. Cl. ................... 514/173; 514/177; 514/178; 514/179; 514/182; 540/23; 540/95; 540/100
[58] Field of Search .............. 514/173, 177, 178, 179, 514/182; 540/23, 95, 100

[56] References Cited

U.S. PATENT DOCUMENTS

| | | | |
|---|---|---|---|
| 3,129,233 | 4/1964 | Deghenghi | 552/651 |
| 4,191,759 | 3/1980 | Johnston et al. | 514/177 |
| 4,317,817 | 3/1982 | Blohm et al. | 514/150 |
| 4,361,578 | 11/1982 | Alig et al. | 514/462 |
| 4,377,584 | 3/1983 | Rasmusson et al. | 514/284 |

OTHER PUBLICATIONS

Hsia and Voight, J. Invest. Dermat. 62:224–227 (1973).
Robaire et al., J. Steroid Biochem. 8:307–310 (1977).
Blohm, T. R., et al., Biochem. Biophys. Res. Comm. 95:273–280 (1980).
Liang, T., et al., J. Steroid Biochem. 19, 385–390 (1983).
Petrow, V., et al., Steroids 38:121–140 (1981).
Cacchi et al., Tet. Letters, 26:1109–1112 (1985).
Neeman, J. Chem. Soc. Perkin I 2297 (1972).
Neeman, J. Chem. Soc. Perkin I 2300 (1972).
Hylarides, J. Org. Chem. 49, 2744 (1984).
Brooks et al., Steroids: 47:1–19 (Jan. 1986).
Ross et al., J. Org. Chem. 29: 2784–2785 (1964).

*Primary Examiner*—Stanley J. Friedman
*Assistant Examiner*—Theodore J. Criares
*Attorney, Agent, or Firm*—Wayne J. Dustman; Stuart R. Suter; Edward T. Lentz

[57] ABSTRACT

Invented are substituted acrylate analogues of steroidal synthetic compounds, pharmaceutical compositions containing these compounds, and methods of using these compounds to inhibit steroid 5-α-reductase. Also invented are intermediates used in preparing these compounds.

68 Claims, No Drawings

STERIOD 5-ALPHA-REDUCTASE INHIBITORS

This is a continuation-in-part of applicants' co-pending application Ser. No. 182,828 filed Apr. 18, 1988, now abandoned, which is a continuation-in-part of applicants' co-pending application Ser. No. 127,147 filed Dec. 1, 1987, now U.S. Pat. No. 4,910,226, which is a continuation-in-part of applicants' application Ser. No. 043,773 filed Apr. 29, 1987, now abandoned.

FIELD OF THE INVENTION

The present invention relates to certain novel substituted acrylate analogues of steroidal synthetic compounds, pharmaceutical compositions containing these compounds, and methods for using these compounds to inhibit mammalian steroid 5-α-reductase.

DESCRIPTION OF RELATED ART

The class of steroidal hormones known as androgens is responsible for the physical characteristics that differentiate males from females. Of the several organs that produce androgens, the testes produce these hormones in the greatest amounts. Centers in the brain exert primary control over the level of androgen production. Numerous physical manifestations and disease states result when ineffective production control results in excessive androgen hormone production. For example, acne vulgaris, seborrhea, female hirsutism, benign prostatic hypertrophy and male pattern baldness are correlated with elevated androgen levels. Additionally, the reduction of androgen levels has been shown to have a therapeutic effect on prostate cancer.

Testosterone is the principal androgen secreted by the testes and is the primary androgenic steroid in the plasma of males. It now is known that 5-α-reduced androgens are the active hormones in some tissues such as the prostate and sebaceous gland. Circulating testosterone thus serves as a prohormone for dihydrotestosterone (DHT), its 5-α-reduced analogue in these tissues but not in others such as muscle and testis. Steroid 5-α-reductase is a NADPH-dependent enzyme that converts testosterone to DHT. The importance of this enzyme in male development was dramatically underscored by discovery of a genetic steroid 5-α-reductase deficiency in male pseudohermaphrodites. Imperato-McGinley, J., et al., (1979), *J. Steroid Biochem.* 11:637–648.

Recognition of the importance of elevated DHT levels in many disease states has stimulated many efforts to synthesize inhibitors of this enzyme. The structures of several known steroid 5-α-reductase inhibitors are shown in Table 1.

TABLE 1

5-α-Reductase Inhibitors

| | | | |
|---|---|---|---|
| (1) | COOH | $K_1 = 1.1 \times 10^{-6}$ M (Reversible) | Hsia and Voight 1973 |
| (2) | | $1 \times 10^{-6}$ M (Irreversible) | Robaire, et al., 1977 |
| (3) | OH | $3.5 \times 10^{-8}$ (Irreversible) | Blohm, et al., 1980 |

TABLE 1-continued

5-α-Reductase Inhibitors (4) 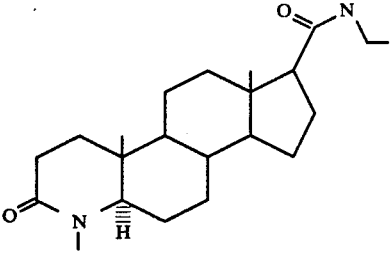 5 × 10⁻⁹ M (Reversible)  Liang, et al., 1983

(5) 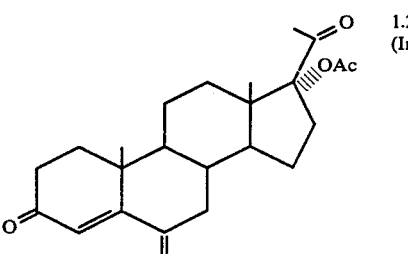 1.25 × 10⁻⁶ M (Irreversible)  Petrow, et al., 1981

The first inhibitor described was the 17-β-carboxylic acid (1) by Hsia and Voight in 1973. *J. Invest. Dermat.* 62:224–227. The secosteroid (2) was the next inhibitor to be described and also has found utility as an affinity label for 5 -α-reductase. Robaire, B., et. al., (1977), *J. Steroid Biochem.* 8:307–310. The diazoketone (3) has been reported as a potent, time-dependent inhibitor of steroid 5-α-reductase. Blohm, T. R., et. al. (1981), *Biochem. Biophys. Res. Comm.* 95:273–280; U.S. Pat. No. 4,317,817, Mar. 2, 1982. Compound (4) is exemplary of a group of 4-aza steroid inhibitors of steroid 5-α-reductase described in U.S. Pat. No. 4,377,584 which issued Mar. 22, 1983, and in Liang, T., et al. (1983), *J. Steroid Biochem.* 19, 385–390. The 6-methylene steroid (5) also has been shown to be a time-dependent inactivator of steroid 5-α-reductase. Petrow, V., et. al. (1981), *Steroids* 38:121–140.

Other steroid 5-α-reductase inhibitors also have been described. U.S. Pat. No. 4,361,578 which issued June 2, 1986, describes a class of homosteroid enzyme inhibitors. U.S. Pat. No. 4,191,759 discloses amides of 17β-carboxy 4-androsten-3 one that are active as steroid 5-α-reductase inhibitors. Japanese Patents J60146855 A and J60116657 A disclose various aniline derivatives having numerous activities including 5-α-reductase inhibiting activity. Japanese Patent I60142941-A discloses phenyl substituted ketones having 5-α-reductase inhibiting activity and European Patent EP173516-A discloses various phenyl substituted amides having similar activity. Shiseido referenced terpene derivatives that are active inhibitors of steroid 5-α-reductase. Japanese Patent No. J59053417-A.

Palladium-catalyzed carbonylation of substituted androstene derivatives has been described. Cacchi, S., et al., (1985), *Tet. Letters* 26:1109 1112. No biological activity for the synthesized compounds, however, is disclosed.

Preparation of steroidal 3-chloro-3,5-dienes has been described by Deghengi, R. and R. Gaudry, *Canadian J. Chem.* (1962) 40:818–820.

Use of phosphorous trihalides to convert steroidal 4-ene-3-keontes to corresponding 3-halo-3,5-dienes has been reported. Ross, J. A. and M. D. Martz, *J. Org. Chem.* (1964) 29:2784–2785.

SUMMARY OF THE INVENTION

The present invention resides in the discovery that steroid 5-α-reductase is inhibited by certain substituted acrylate analogues of steroidal synthetic compounds. The compounds are potent enzyme inhibitors.

Presently preferred compounds of the invention and compounds used in the invented -pharmaceutical compositions and the invented methods include:

20-α-(hydroxymethyl)-5-α-pregn-3 ene-3-carboxylic acid,

N,N-diisopropyl-5-α-androst 3-ene 17β-carboxamide-3-carboxylic acid,

N,N-diisopropyl-androst-3,5-diene-17β-carboxamide-3-carboxylic acid,

17β-(N,N-diisopropylcarboxamide)-4-fluoro-5-α-androst-3-ene-3-carboxylic acid,

20-α-(hydroxymethyl)-4-fluoro-5-α-pregn-3-ene-3-carboxylic acid,

17β-N,N-diisopropylcarboxamide-5-α-androst-1,3-diene-3-carboxylic acid,

N-t-Butyl Androst 3,5-diene-17β-carboxamide-3-carboxylic acid,

N,N-Diisopropyl 5-α-Androst-2-ene-17β-carboxamide-3-carboxylic acid,

N,N-Diisopropyl Androst-2,4,-diene-17β-carboxamide-3-carboxylic acid,

N,N-Diisopropyl 5-α-Androstane-17β-carboxamide-3β-carboxylic acid,

N,N-Diisopropyl Estr-3,5(10)-diene-17β-carboxamide-3-carboxylic acid,

N,N-Diisopropyl Estr-3,5-diene-17β-carboxamide-3-carboxylic acid,

17β-(N,N-Diisopropylcarboxamide)-androst-3,5,11-triene-3-carboxylic acid,

17β-(N,N-Diisopropylcarboxamide)-androst-3,5-diene-3-thiocarboxylic acid,

17β-(N-t-Butylcarboxamide)-androst-3,5,11-triene-3-carboxylic acid, and

17-β-(N,t-Butylcarboxamide)-androst-3,5-diene-3-thiocarboxylic acid.

In a further aspect of the invention there are provided novel intermediates and novel processes useful in preparing the presently invented 5-α-reductase inhibiting compounds.

The invention also is a method for inhibiting 5-α-reductase activity in mammals, including humans, that comprises administering to a subject in need thereof an effective amount of a presently invented 5-α-reductase inhibiting compound.

Included in the present invention are pharmaceutical compositions comprising a pharmaceutical carrier and compounds useful in the methods of the invention.

DETAILED DESCRIPTION OF THE INVENTION

The presently invented compounds that inhibit 5-α-reductase have the following Formula (I):

(I)

in which:

The A ring has up to 2 double bonds;

The B, C, and D rings have optional double bonds where indicated by the broken lines, provided that the A-B rings and the B-C rings do not have adjacent double bonds and the D ring does not have a $C_{16}$–$C_{17}$ double bond when $R^3$ represents two substituents or a divalent substituent;

M is O or S;

Z is $CH_2$ or, when part of a double bond, CH;

X is H, Cl, F, Br, I, $CF_3$, or $C_{1-6}$alkyl;

Y is H, $CF_3$, F, or Cl, $CH_3$, provided that Y is H when there is no $C_5$–$C_6$ double bond;

$R^1$ is H or $C_{1-8}$alkyl;

$R^2$ is absent or present as H or $CH_3$ provided $R^2$ is absent when the carbon to which it is attached is double bonded;

$R^{10}$ is absent when there is a $C_4$–$C_5$, $C_5$–$C_6$, or $C_5$–$C_{10}$ double bond, or present as an alpha hydrogen; and $R^3$ is (1) α-hydrogen, α-hydroxyl, or α-acetoxy and/or (a)

$$\beta\text{-W}-\overset{\overset{\displaystyle O}{\|}}{C}-R^4$$

where W is a bond or $C_{1-12}$alkyl, and $R^4$ is
(i) hydrogen,
(ii) hydroxyl,
(iii) $C_{1-8}$alkyl,
(iv) hydroxy $C_{1-8}$alkyl,
(v) $C_{1-8}$alkoxy,
(vi) $NR^5R^6$, where $R^5$ and $R^6$ are each independently selected from hydrogen, $C_{1-8}$-alkyl, $C_{3-6}$cycloalkyl, phenyl; or $R^5$ and $R^6$ taken together with the nitrogen to which they are attached represent a 5–6 membered saturated ring comprising up to one other heteroatom selected from oxygen and nitrogen, or
(vii) $OR^7$, where $R^7$ is hydrogen, alkali metal, $C_{1-18}$alkyl, benzyl, or (b) β-Alk-$OR^8$, where Alk is $C_{1-12}$alkyl, and $R^8$ is
(i) phenyl$C_{1-6}$alkylcarbonyl,
(ii) $C_{5-10}$cycloalkylcarbonyl,
(iii) benzoyl,
(iv) $C_{1-8}$alkoxycarbonyl,
(v) aminocarbonyl, or $C_{1-8}$ alkyl substituted aminocarbonyl,
(vi) hydrogen, or
(vii) $C_{1-8}$alkyl, (2) =CH—W—CO—$R^4$ or =CH—W—$OR^8$, where W is a bond or $C_{1-12}$alkyl and $R^4$ and $R^8$ have the same meaning as above and $R^8$ also is hydrogen or $C_{1-20}$-alkylcarbonyl;

where the dashed bond replaces the 17-α-hydrogen, (4) α-hydrogen and β-$NHCOR^9$ where $R^9$ is $C_{1-12}$alkyl or β-$NR^5R^6$ where $R^5$ and $R^6$ have the same meaning as above, (5) α-hydrogen and β-cyano, (6) α-hydrogen and β-tetrazolyl, or (7) keto;

or a pharmaceutically acceptable salt thereof; except compounds in which:

The A ring has a $C_3$–$C_4$ double bond, the B ring has a $C_5$–$C_6$ double double bond, $R^1$ is $CH_3$, and $R^3$ is keto;

The A ring has a $C_3$–$C_4$ double bond, the B ring has a $C_5$–$C_6$ double bond and the D ring has a $C_{16}$–$C_{17}$ double bond, $R^1$ is $CH_3$, and $R^3$ is $COOCH_3$; and The B ring has a $C_5$–$C_6$ double bond, $R^1$ is $CH_3$, and $R^3$ is $COCH_3$.

As used herein, unless otherwise specified, $C_{l-n}$alkyl and $C_{l-n}$alk means a straight or branched hydrocarbon chain having 1 to n carbons and Alk means a straight or branched hydrocarbon chain having 1 to 12 carbons.

Also, preferred among the presently invented compounds are those having Formula (II):

(II)

in which:

The A ring has up to 2 double bonds;

The B and C rings have optional double bonds where indicated by the broken lines, provided that the A B rings do not have adjacent double bonds;

M is O or S;

X is H or halo, $R^1$ is H or $C_{1-8}$alkyl;

$R^2$ is absent or present as H or $CH_3$, provided $R^2$ is absent when the carbon to which it is attached is double bonded;

$R^{10}$ is absent when there is a $C_4$-$C_5$, $C_5$-$C_6$, or $C_5$-$C_{10}$ double bond, or present as an alpha hydrogen; and $R^{13}$ is (a) $CH(CH_3)CH_2OR^{20}$ wherein $R^{20}$ is H or $C_{1-6}$alkyl, or (b) $CONR^{21}R^{22}$ wherein $R^{21}$ and $R^{22}$ independently are H or $C_{1-8}$ alkyl. Particularly preferred are Formula (II) compounds in which the A ring has a $C_3$-$C_4$ double bond.

Also preferred among the presently invented compounds are those having Formula (IIa):

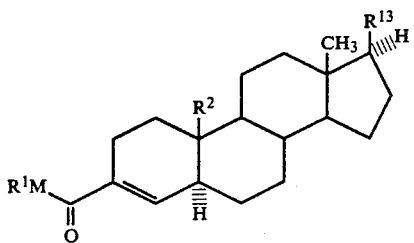

in which $R^1$, $R^2$ and $R^{13}$ are as in Formula (II) and M is O or S.

Additionally, preferred among the presently invented compounds are those having the Formula (IIb):

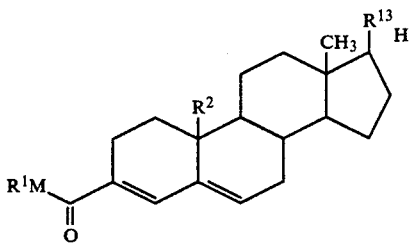

in which $R^1$, and $R^2$ and $R^{13}$ are as in Formula (II) and M is O or S.

Compounds of Formula (III) are included in the pharmaceutical compositions of the invention and used in the methods of the invention.

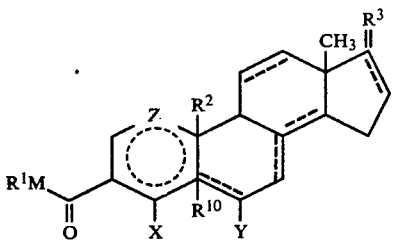

in which:

The A ring has up to 2 double bonds;

The B, C, and D rings have optional double bonds where indicated by the broken lines, provided that the A-B rings and the B-C rings do not have adjacent double bonds and the D ring does not have a $C_{16}$-$C_{17}$ double bond when $R^3$ represents two substituents or a divalent substituent;

M is O or S;

Z is $CH_2$ or, when part of a double bond, CH;

X is H, Cl, Br, F, I, $CF_3$, or $C_{1-6}$alkyl;

Y is H, $CF_3$, F, or Cl, $CH_3$, provided that Y is H when there is no $C_5$-$C_6$ double bond;

$R^1$ is H or $C_{1-8}$ alkyl; $R^2$ is absent or present as H or $CH_3$, provided $R^2$ is absent when the carbon to which it is attached is double bonded; $R^{10}$ is absent when there is a $C_4$-$C_5$, $C_5$-$C_6$, or $C_5$-$C_{10}$ double bond, or present as an alpha hydrogen; and $R^3$ is (1) α-hydrogen, α-hydroxyl, or α-acetoxy and/or (a)

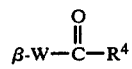

where W is a bond or $C_{1-12}$alkyl, and $R^4$ is (i) hydrogen, (ii) hydroxyl, (iii) $C_{1-8}$alkyl, (iv) hydroxy $C_{1-8}$alkyl, (v) $C_{1-8}$alkoxy, (vi) $NR^5R^6$, where $R^5$ and $R^6$ are each independently selected from hydrogen, $C_{1-8}$-alkyl, $C_{3-6}$cycloalkyl, phenyl; or $R^5$ and $R^6$ taken together with the nitrogen to which they are attached represent a 5-6 membered saturated ring comprising up to one other heteroatom selected from oxygen and nitrogen, or (vii) $OR^7$, where $R^7$ is hydrogen, alkali metal, $C_{1-18}$alkyl, benzyl, or (b) β-Alk-$OR^8$, where Alk is $C_{1-12}$alkyl, and $R^8$ is (i) phenyl$C_{1-6}$alkylcarbonyl, (ii) $C_{5-10}$cycloalkylcarbonyl, (iii) benzoyl, (iv) $C_{1-8}$alkoxycarbonyl, (v) aminocarbonyl, or $C_{1-8}$alkyl substituted aminocarbonyl, (vi) hydrogen, or (vii) $C_{1-8}$alkyl, (2) $=CH-W-CO-R^4$ or $=CH-W-OR^8$, where W is a bond or $C_{1-12}$alkyl, and $R^4$ and $R^8$ have the same meaning as above and $R^8$ also is hydrogen or $C_{1-20}$alkylcarbonyl;

(3)

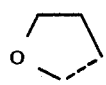

where the dashed bond replaces the 17-α-hydrogen, (4) α-hydrogen and β-$NHCOR^9$ where $R^9$ is $C_{1-12}$ alkyl or β-$NR^5R^6$ where $R^5$ and $R^6$ have the same meaning as above, (5) α-hydrogen and β-cyano, (6) α-hydrogen and β-tetrazolyl, or (7) keto;

or a pharmaceutically acceptable salt thereof.

As used above and throughout the remainder of the specification and claims the carbons of the steriod nucleus are numbered and the rings and lettered as follows:

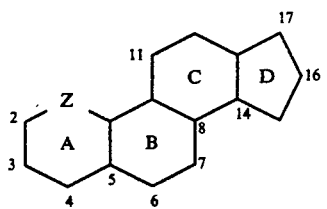

Formula (III) compounds are prepared as shown in Schemes I through VIII wherein $R^2$ and X are as defined in Formula (III). $R^{14}$ is $R^3$ or moieties which can be converted to those of $R^3$ by known chemical reactions such as described in J. Fried and J. Edwards, Organic *Reactions in Steroid Chemistry*, Pub: Van Nostrand Reinhold Company (1972) provided that $R^{14}$ does not include any such moieties that render inoperative the Schemes I to VIII processes. As demonstrated in the following Examples, reactions to convert to $R^{14}$ to $R^3$ are performed on products of the synthetic pathways of Schemes I through VIII or, where appropriate or preferable, on certain intermediates in these synthetic pathways.

such as dibromoethane, bromobenzene, or, preferably isoprene, and evaporated to form a residue. Formula (b) compounds then are prepared by reacting the residue dissolved in a suitable organic solvent, preferably THF, with an N-aryltrihaloalkyl sulfonimide, preferably N phenyltrifluoromethylsulfonimide at a temperature of −20° C. to 20° C.

Formula (c) compounds are prepared by adding to a formula (b) compound dissolved in a suitable organic solvent such as dimethylformide (DMF) an organic base such as timethylamine, or, preferably, triethylamine, a phosphine such as bis(diphenylphosphino)propane, or, preferably triphenylphosphine, a palladium(II) compound such as palladium(II) chloride, or, preferably, palladium(II) acetate, and a $C_{1-6}$alkyl alcohol ($C_{1-6}$alkOH), followed by addition of carbon monoxide (CO). Addition of a strong base such as sodium hydroxide, potassium hydroxide, or, preferably, lithium hydroxide to a formula (c) compound dissolved in a suitable organic solvent such as THF and methanol followed by addition of strong acid, preferably, hydrochloric acid yields formula (d) compounds.

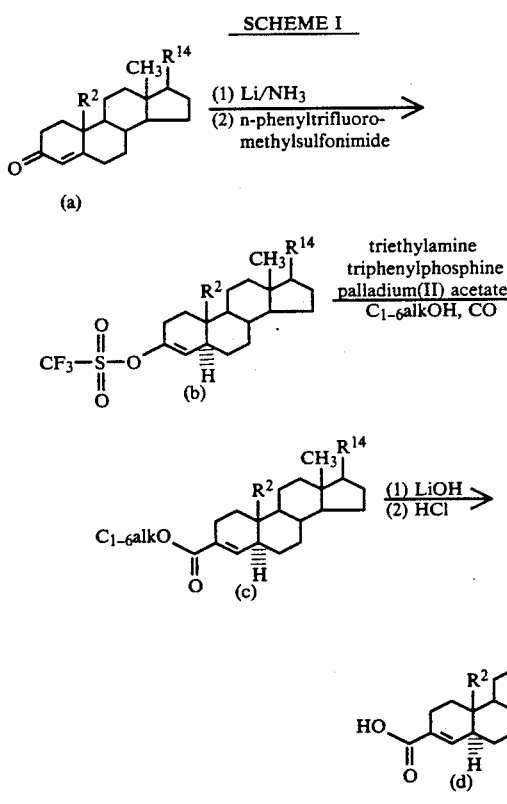

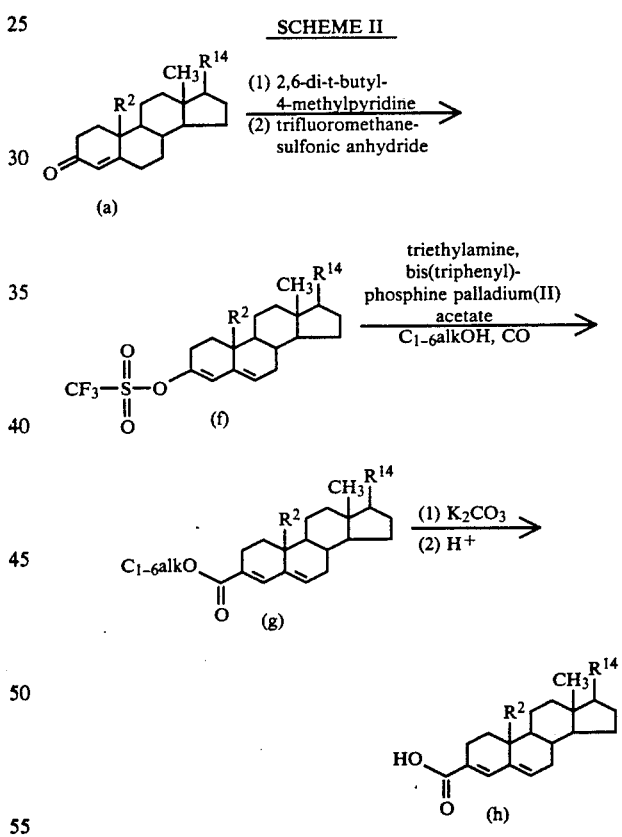

Scheme I depicts formation of Formula (III) compounds having a double bond is at $C_3$–$C_4$, X is H, and n is 1. The starting 4 ene-3-one compounds are known and readily available and are synthesized from available precursors using known procedures. According to Scheme I, a solution of a 4-ene 3 one compound (a) and a suitable organic proton donor such as t butanol, or, preferably aniline in an appropriate organic solvent, preferably tetrahydrofuran (THF) are added to a reducing metal amine, preferably a lithium/ammonia ($Li/NH_3$) solution, to form a reaction mixture. This reaction mixture is stirred at −100° C. to −30° C., preferably −78° C., quenched with a lithium scavenger Scheme II outlines synthesis of Formula (III) compounds wherein there is a $C_5$–$C_6$ double bond. The starting materials are the formula (a) 4-ene-3-one compounds from Scheme I. According to Scheme II, to a formula (a) compound dissolved in an appropriate organic solvent, preferably methylene chloride, is added 2,6-di-t-butyl-4-methylpyridine. A trihaloalkyl sulfonic anhydride, preferably trifluoromethane sulfonic anhydride then is added to yield formula (f) compounds. To formula (f) compounds dissolved in a suitable organic solvent such as DMF an organic base such as trimethylamine, or, preferably, triethylamine, a palladium(II)

compound such as bis(diphenylphosphino)propane, palladium(II) acetate, or, preferably bis(triphenylphosphine)palladium(II) acetate, and a $C_{1-6}$alkOH followed by addition of CO to give formula (g) compounds. Salts of formula (h) compounds then are prepared by hydrolyzing with a strong base such as sodium hydroxide, lithium hydroxide, potassium hydroxide, or, preferably, potassium carbonate the formula (g) ester compounds. Formula (h) free acids are prepared by treating the salts with a strong acid such as hydrochloric, sulfuric, or hydrobromic acids.

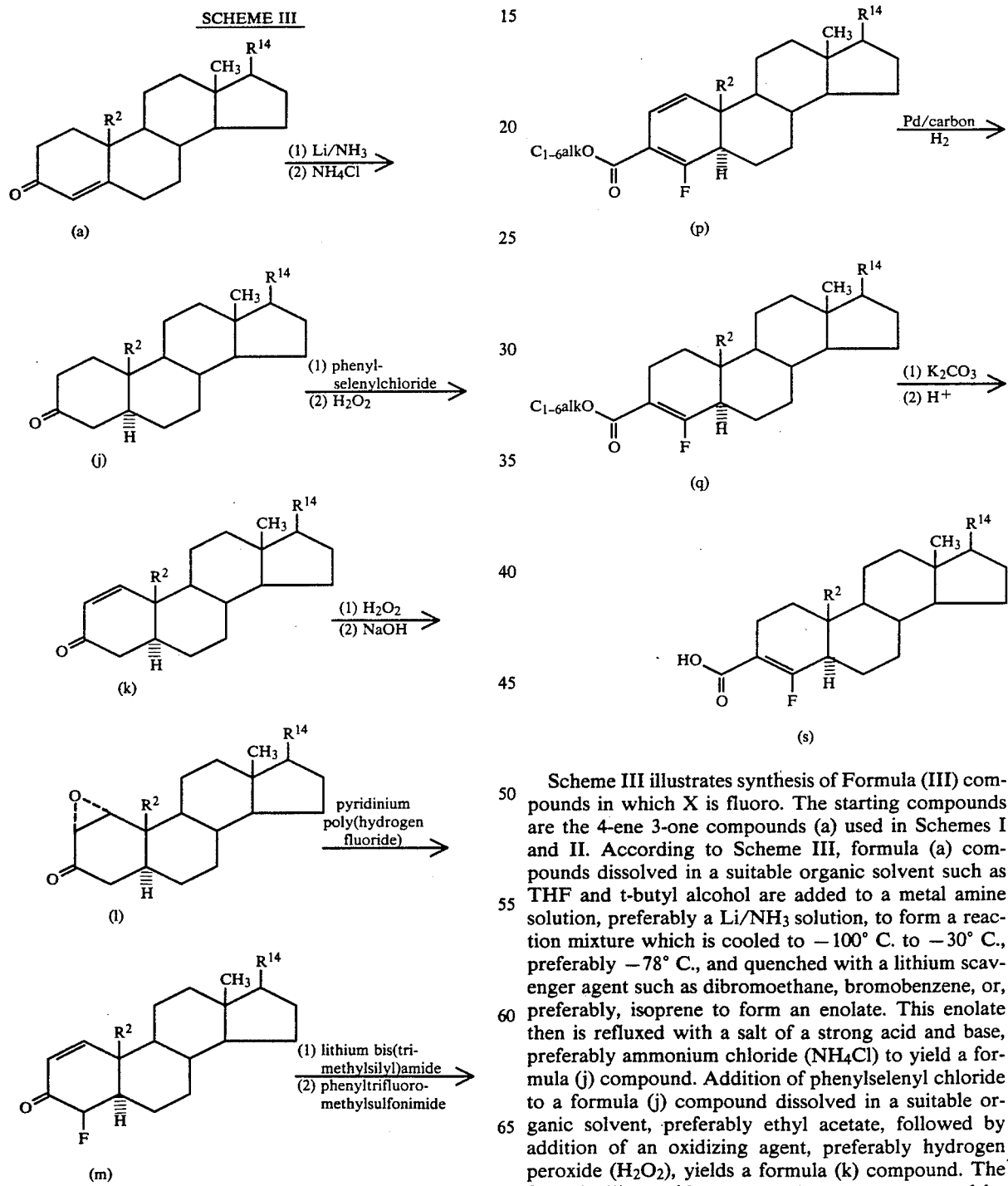

Scheme III illustrates synthesis of Formula (III) compounds in which X is fluoro. The starting compounds are the 4-ene 3-one compounds (a) used in Schemes I and II. According to Scheme III, formula (a) compounds dissolved in a suitable organic solvent such as THF and t-butyl alcohol are added to a metal amine solution, preferably a Li/NH$_3$ solution, to form a reaction mixture which is cooled to $-100°$ C. to $-30°$ C., preferably $-78°$ C., and quenched with a lithium scavenger agent such as dibromoethane, bromobenzene, or, preferably, isoprene to form an enolate. This enolate then is refluxed with a salt of a strong acid and base, preferably ammonium chloride (NH$_4$Cl) to yield a formula (j) compound. Addition of phenylselenyl chloride to a formula (j) compound dissolved in a suitable organic solvent, preferably ethyl acetate, followed by addition of an oxidizing agent, preferably hydrogen peroxide (H$_2$O$_2$), yields a formula (k) compound. The formula (l) epoxide compounds next are prepared by addition of an oxidizing agent, preferably $H_2O_2$, to a formula (k) compound dissolved in a suitable organic solvent, preferably methanol, cooled to 5° C. to 25° C., preferably 15° C., followed by addition of a strong base such as NaOH.

Formula (l) compounds then are dissolved in a suitable organic solvent, preferably THF, and cooled to −20° C. to 0° C., and a fluorinating agent such as hydrogen fluoride, or, preferably, pyridinium poly(hydrogen fluoride) is added to yield formula (m) compounds in which X is fluoro. Formula (m) compounds are dissolved in a suitable organic solvent such as THF followed by addition to a solution of a metalloamide base such as lithium diisopropylamide or, preferably lithium bis(trimethylsilyl)amide in a suitable organic solvent such as THF. To this reaction mixture then is added a triflating agent such as trifluoromethanesulfonic anhydride, or, preferably, N phenyltrifluoromethanesulfonimide to yield formula (o) compounds.

Formula (p) compounds then are synthesized by adding to a formula (o) compound dissolved in a suitable organic solvent such as DMF an organic base such as timethylamine, or, preferably, triethylamine, a phosphine such as bis(diphenylphosphino)propane, or, preferably triphenylphosphine, and a palladium(II) compound such as palladium(II) chloride, or, preferably, palladium(II) acetate followed by addition of CO. Hydrogenation of formula (p) compounds dissolved in a suitable organic solvent such as ethyl acetate and hexane using an appropriate hydrogenation agent such as platinum dioxide, Raney nickel, or, preferably palladium on carbon (Pd/carbon) yields formula (q) compounds. Hydrolysis of the ester with a base such as sodium hydroxide, potassium hydroxide, lithium hydroxide, or, preferably potassium carbonate dissolved in an aqueous $C_{1-6}$alkyl alcohol solution, preferably methanol yields a salt of a formula (s) compound. Treatment of the salt with strong acid yields a formula (s) compound.

Formula (s) compounds in which X is other than hydrogen or fluoro are prepared using processes such as exemplified in Examples 20, 21, and 22.

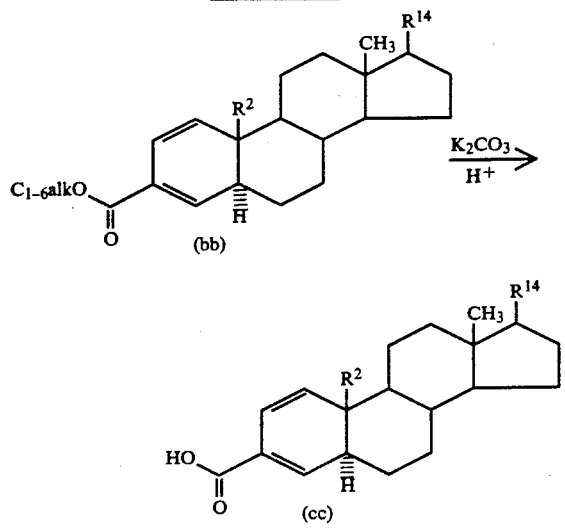

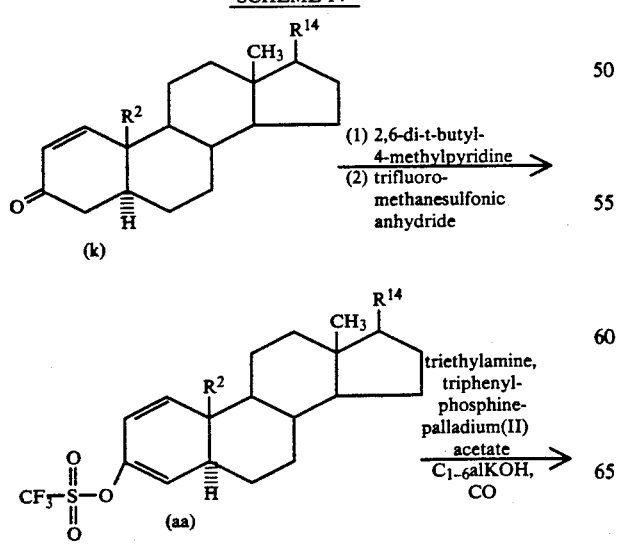

Scheme IV outlines formation of Formula (III) compounds wherein there is a $C_1$–$C_2$ double bond. The starting materials in Scheme IV are formula (k) compounds prepared as described in Scheme III. According to Scheme IV, formula (aa) compounds are prepared using the processes used in making formula (f) compounds of Scheme II. Next formula (bb) compounds are prepared by the reactions employed to form formula (c) compounds in Scheme I. Thereafter, treatment of formula (bb) compounds as described in forming formula (s) compounds of Scheme III yields formula (cc) compounds.

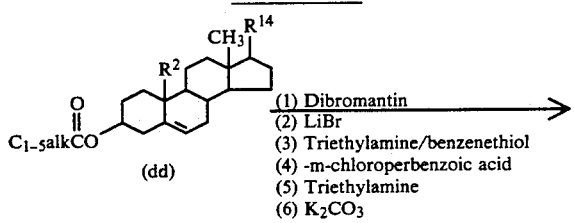

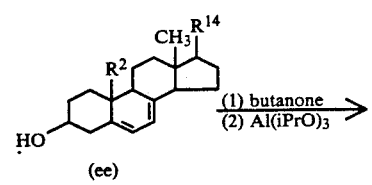

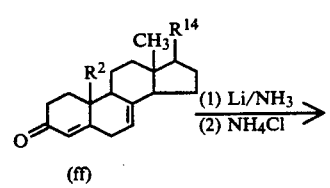

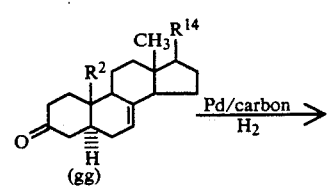

-continued
SCHEME V

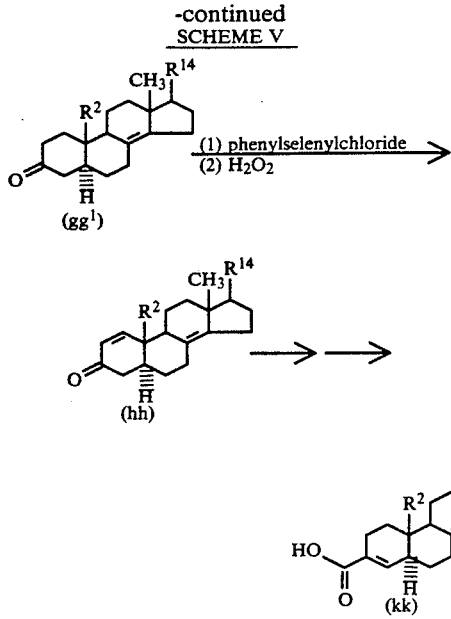

Scheme V shows synthesis of Formula (III) compounds in which there is a $C_8$-$C_{14}$ double bond. The formula (dd) starting materials are known and available and can be synthesized from available materials using known methods. Formula (ee) compounds are prepared by first treatint formula (dd) compounds in a suitable organic solvent such as hexane with a brominating agent such as N bromosuccinamide, or, preferably dibromantin and a mild base, preferably sodium bicarbonate, and heated, preferably at reflux. Thereafter, the mixture is treated with lithium bromide (LiBr), cooled to −20° C. to 20° C., preferably 0° C., and treated with triethylamine and benzenethiol. Treatment with an oxidazing agent such as sodium periodate, hydrogen peroxide, or preferably m-chloroperbenzoic acid follows and is followed by heating to 40° C. to 100° C., preferably 70° C., and treatment with an organic base such as trimethylamine, or preferably triethylamine. Treatment with a strong base such as sodium hydroxide, potassium hydroxide, lithium hydroxide, or, preferably, potassium carbonate yields formula (ee) compounds.

Formula (ee) compounds then are dissolved in a suitable organic solvent, preferably toluene, and treated with an alkyl ketone agent such as a cyclohexanone, or, preferably butanone followed by treatment with aluminum isopropoxide and heating, preferably at reflux, to prepare formula (ff) compounds. Reaction of formula (ff) compounds as described in forming Scheme III, formula (j) compounds yields formula (gg) compounds.

Hydrogenation of formula (gg) compounds using suitable catalysts such as platinium dioxide, Raney nickel, or, preferably Pd/carbon, yields formula (gg') compounds. Formula (hh) compounds there are prepared by adding phenylselenyl chloride to a formula (gg') compound dissolved in a suitable organic solvent, preferably ethyl acetate, followed by addition of an oxidizing agent, preferably $H_2O_2$. Substitution of formula (hh) compounds for formula (m) compounds in Scheme III yields formula (kk) compounds.

SCHEME VI

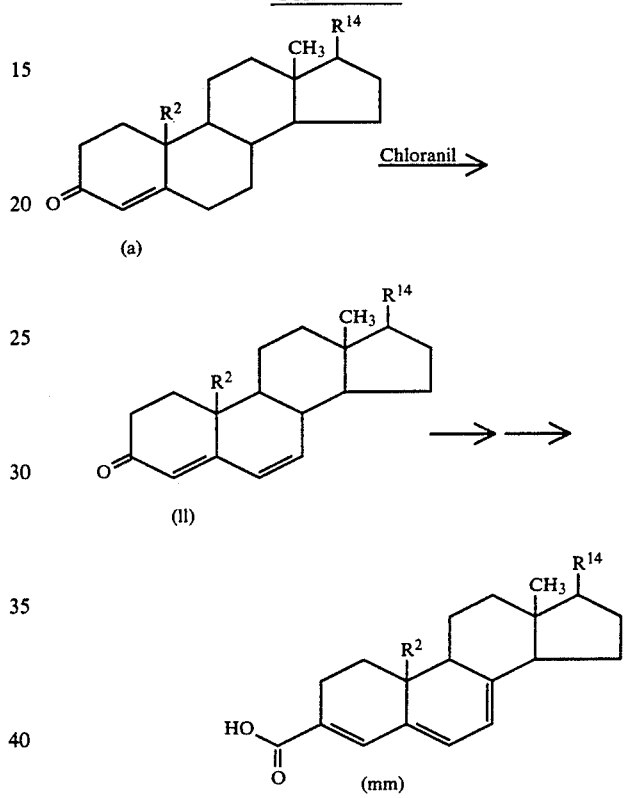

Scheme VI outlines formation of Formula (III) compounds in which there is a $C_5$-$C_6$ and $C_7$-$C_8$ double bond from Scheme I, formula (a) compounds. Treatment of formula (a) compounds in a suitable solvent such as t butanol with chloranil, with heating, preferably at reflux, yields formula (11) compounds. Thereafter, substituting formula (11) compounds for formula (a) compounds in the Scheme II process yields formula (mm) compounds.

SCHEME VII

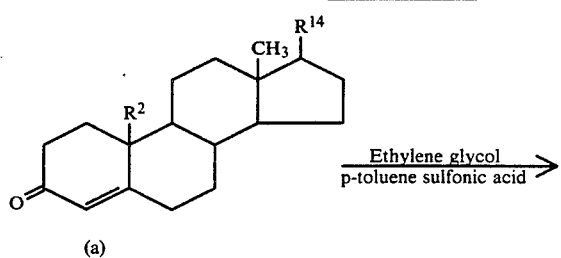

SCHEME VII

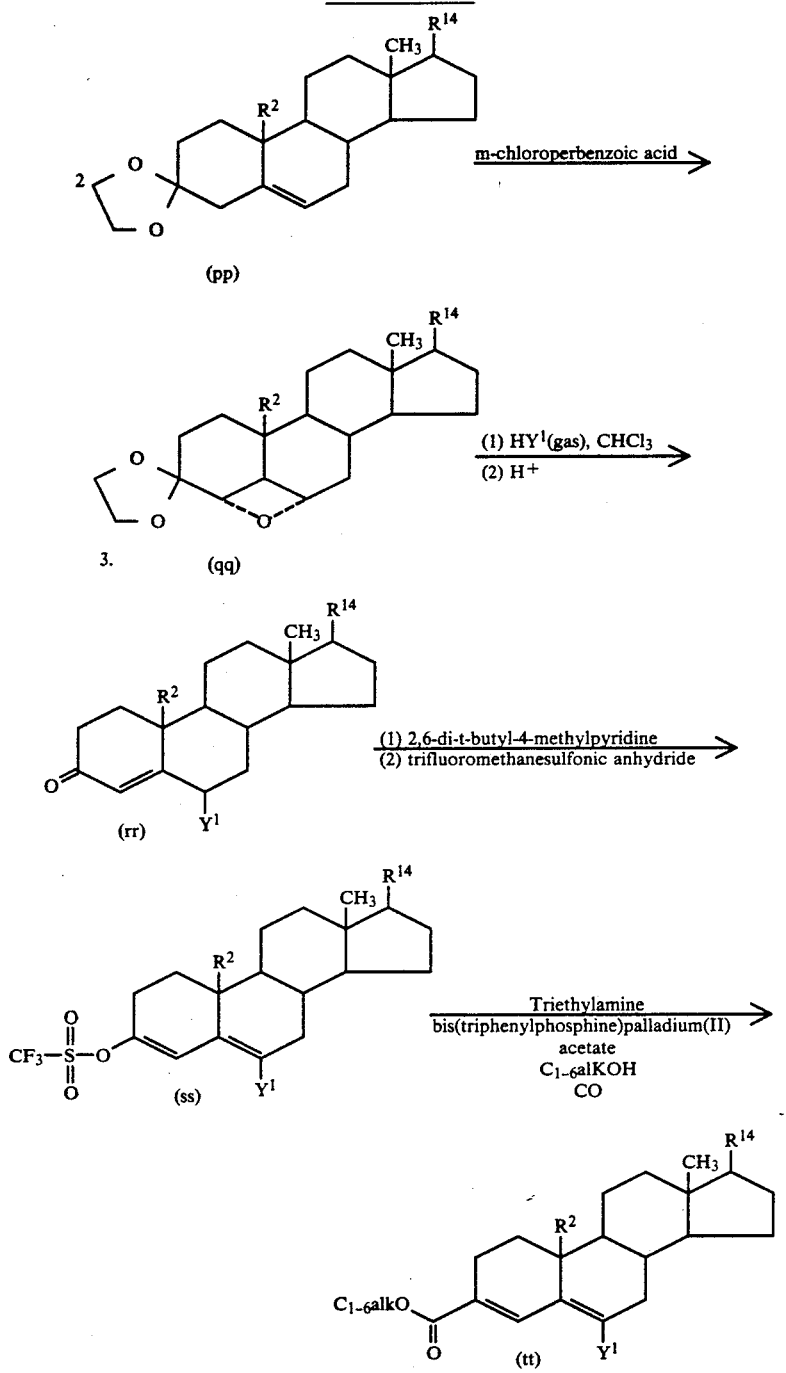

Scheme VII outlines formation of Formula (III) compounds in which Y is chloro or fluoro ($Y^1$) from Scheme I, formula (a) compounds. Formula (pp) compounds are prepared by reacting formula (a) compounds with a suitable keto group protecting agent such as ethylene glycol in the presence of an acid catalyst such as p-toluene sulfonic acid. Treatment of formula (pp) compounds with a suitable oxidizing agent, preferably m-chloroperbenzoic acid in a suitable organic solvent such as dichloromethane yields formula (qq) epoxide compounds.

Formula (rr) compounds then are prepared by adding gaseous hydrogen fluoride or hydrogen chloride to a formula (qq) compound in a suitable organic solvent such as chloroform, or (where $Y^1 = F$) by adding boron-tri-fluoride-etherate to a formula (qq) compound in a suitable organic solvent, prferably benzene:ether followed by treatment with strong acid, preferably hydrogen chloride in glacial acetic acid. Next, 2,6 di-t-butyl 4-methylpyridine followed by trifluoromethanesulfonic anhydride are added to a formula (rr) compound to yield a formula (ss) compound. Reaction of a formula (ss) compound in a suitable organic solvent, preferably dimethylformamide, with triethylamine, a $C_{1-6}$alKOH, bis(triphenylphosphine)palladium(II) acetate, and carbon monoxide yields formula (tt) compounds. The free acids of formula (tt) optionally are prepared by processes shown in the preceding schemes. Compounds of Formula (I) in which Y is trifluoromethyl are prepared by processes such as exemplified in Example 23.

Compounds having a double bond at $C_{11}$ are prepared by modifications of the Schemes I through VIII by procedures which would be apparent to those skilled in the art and are exempliefied in Example 31, below.

Compounds of Formula (III) wherein M is sulfur are prepared from Formula (III) compounds wherein M is oxygen using known procedures such as shown in Example 33 below.

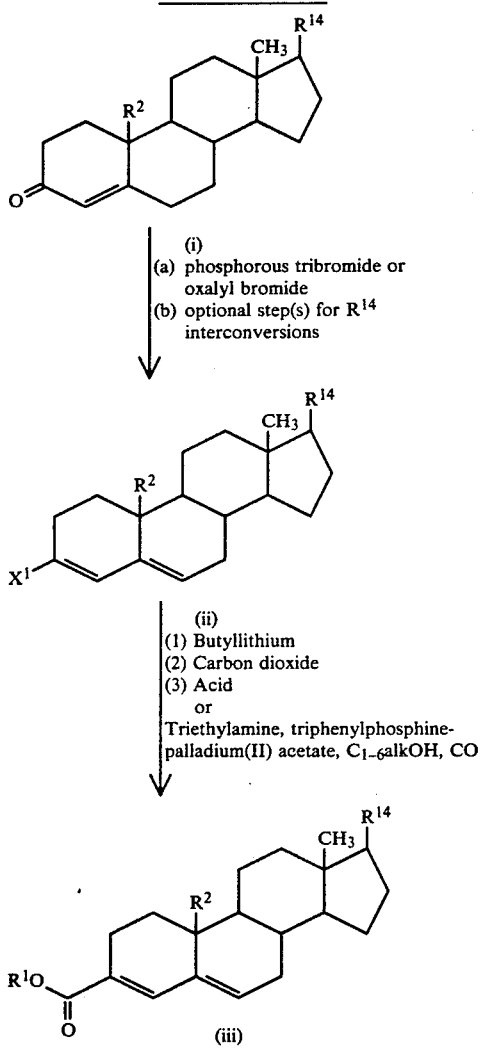

SCHEME VIII (i)
(a) phosphorous tribromide or oxalyl bromide
(b) optional step(s) for $R^{14}$ interconversions (ii)
(1) Butyllithium
(2) Carbon dioxide
(3) Acid
or
Triethylamine, triphenylphosphine-palladium(II) acetate, $C_{1-6}alkOH$, CO (iii)

Scheme VIII shows a preferred synthetic method for preparing Formula (III) compounds having double bonds at $C_3$–$C_4$ and $C_5$–$C_6$. The starting materials are the formula (a) 4-ene-3-one compounds from Scheme I. $X^1$ is bromo, or chloro, or iodo. According to Scheme VIII, formula (i) compounds are treated with a carboxylic acid halide such as acetyl chloride, acetyl bromide, oxalyl chloride, or preferably, oxalyl bromide to yield formula (ii) compounds. Alternatively, formula (ii) compounds are prepared by treating formula (i) compounds with a phosphorus trihalide, or phosphorous pentahalide, such as phosphoryl chloride, phosphorous pentachloride or preferably phosphorous tribromide, in acid, preferably acetic acid. Included in this process may be desired interconversions among the various groups comprising $R^{14}$ using standard procedures known to organic chemists, especially conversion of esters to carboxylic acids, then to acid halides and the to carboxamides.

Formula (iii) compounds, Formula (III) compounds unsaturated at $C_3$–$C_4$ and $C_5$–$C_6$, then are prepared by adding an alkyllithium reagent such as n-butyllithium, s-butyllithium or t-butyllithium to a compound (ii) followed by treatment with a carboxylating agent such as diethyl carbonate, ethyl chloroformate, or, preferably, carbon dioxide. Alternatively, such formula (iii) compounds are prepared by adding a palladium catalyst, preferably triphenylphosphine palladium (II) acetate in the presence of a base, preferably triethylamine and a $C_{1-6}$ alcohol, preferably methanol, under an atmosphere of carbon monoxide.

Scheme VIII shows preparation of Formula (III) compounds in which X and Y are hydrogen. Scheme VIII is used to prepare Formula (III) compounds in which X or Y is other than hydrogen by replacing the formula (i) starting materials with appropriately substituted alternates. Compounds are selected so that they can be converted by known procedures to the $R^2$ and $R^3$ groups of the target Formula (III) compounds by additional steps in the synthetic process, as stated above, for example.

In the above Schemes, the starting materials are selected so that the $R^2$ and $R^{14}$ groups in the formula (a) compound are the same as the $R^2$ and $R^3$ groups in the Formula (III) compound being synthesized. Alternatively, the $R^2$ and $R^{14}$ groups of the formula (a) compound are selected so that they can be converted by known procedures to the $R^2$ and $R^3$ groups of the target Formula (III) compound by additional steps in the synthetic process. For example, Formula (III) compounds wherein $R^3$ is carboxylic acid are converted to the corresponding amides by reaction with amines or substituted amines via the corresponding acid chlorides. Similarly, Formula (III) compounds wherein $R^3$ is $CH_3CHCOOH$ is prepared by oxidation of the corresponding alcohol. In addition to the above schemes, Formula (III) compounds are prepared according the process of example 25A.

Pharmaceutically acceptable acid addition salts of the compounds of the invention containing a basic group are formed where appropriate with strong or moderately strong organic or inorganic acids in the presence of a basic amine by methods known to the art. For example, the base is reacted with an inorganic or organic acid in an aqueous miscible solvent such as ethanol with isolation of the salt by removing the solvent or in an aqueous immiscible solvent when the acid is soluble therein, such as ethyl ether or chloroform, with the desired salt separating directly or isolated by removing the solvent. Exemplary of the acid addition salts which are included in this invention are maleate, fumarate, lactate, oxalate, methanesulfonate, ethanesulfonate, benzenesulfonate, tartrate, citrate, hydrochloride, hydrobromide, sulfate, phosphate and nitrate salts. Pharmaceutically acceptable base addition salts of compounds of the invention containing an acidic group are prepared by known methods from organic and inorganic bases include nontoxic alkali metal and alkaline earth bases, for example, calcium, sodium, and potassium hydroxide; ammonium hydroxide, and nontoxic organic bases such as triethylamine, butylamine, piperazine, and (trihydroxymethyl)methylamine.

In preparing the presently invented compounds of Formula (III), novel intermediates of the following Formula (IV) are synthesized;

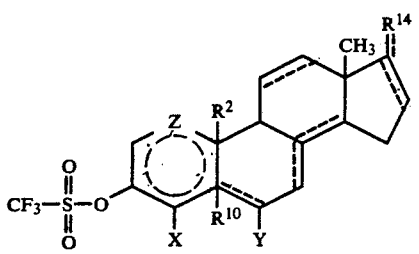

in which:

The A, B, C, and D ring double bonds, X, Y, Z, $R^2$ and $R^{10}$ are as defined in Formula (III) and $R^{14}$ is $R^3$ as defined in Formula (III) or moieties which can be converted to those of $R^3$ by known chemical reactions such as described in J. Fried and J. Edwards, *Organic Reactions in Steroid Chemistry*, Pub: Van Nostrand Reinhold Company (1972).

Also prepared in synthesizing the presently invented formula (III) compounds were novel intermediates of the formula (VI):

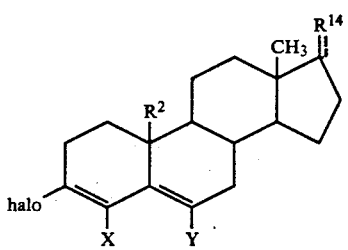

in which:

The A, B, C, and D ring double bonds, X, Y, Z, $R^2$ and $R^{14}$ are as defined in Formula (IV).

Because the pharmaceutically active compounds of the present invention steroid 5-α-reductase activity, they have therapeutic utility in treating diseases and conditions wherein decreases in DHT activity produce the desired therapeutic effect. Such diseases and conditions include acne vulgaris, seborrhea, female hirsutism, prostate diseases such as benign prostatic hypertrophy and prostatic adenocarcinoma and male pattern baldness. The potency of several compounds of the invention was tested for potency in inhibiting human steroid 5-α-reductase using tissue from hyperplastic human prostates. In determining potency in inhibiting the human enzyme, the following procedure was employed:

Frozen human prostates were thawed and minced into small pieces (5 mm³). The tissue was homogenized in 3 to 5 volumes of 20 mM potassium phosphate, pH 6.5, buffer containing 0.33 M sucrose, 1 mM dithiothreitol, and 50 μM NADPH with a Brinkmann Polytron (Sybron Corporation, Westbury, N.Y.). The solution was subjected to sonication for 3 to 5 minutes with a Sonifier Branson Sonic Power Co.) followed by hand homogenization in a glass-to-glass Dounce homogenizer (Kontes Glass Company, Vineland, N.J.).

Prostatic particles were obtained by differential centrifugation at 600 or 1,000 x g for 20 minutes and 140,000 x g for 60 minutes at 4° C. The pellet obtained from the 140,000 x g centrifugation was washed with 5 to 10 tissue volumes of the buffer described above and recentrifuged at 140,000 x g. The resulting pellet was suspended in 20 mM potassium phosphate buffer, pH 6.5, containing 20% glycerol, 1 mM dithiothreitol, and 50 μM NADPH. The suspended particulate solution was stored at −80° C.

A constant amount of [$^{14}$C]-testosterone (52 to 55 mCi/mmol, New England Nuclear, Boston, MA) in ethanol and varying amounts of the potential inhibitor in ethanol were deposited in test tubes and concentrated to dryness in a SAVANT Speed Vac. To each tube was added buffer, 20 μl of 10 mM NADPH and an aliquot of prostatic particulate solution to a final volume of 1.0 ml of 50 mM sodium citrate, pH 5.0. After incubating the solution at 37° C. for 20 to 30 minutes the reaction was quenched by the addition of 4 ml ethyl acetate and 0.25 μmol each of testosterone, dihydrotestosterone, androstanediol, and androstanedione as carriers. The organic layer was removed to a second test tube and evaporated to dryness in a Speed Vac. The residue was dissolved in 20 to 30 μl chloroform, spotted on an individual lane of a 20 x 20 cm prechannelled silica gel TLC plate (Si 250F PA, Baker Chemical) and developed twice with acetone:chloroform (1:9). The radiochemical content in the bands of the substrate and the products was determined with a BIOSCAN Imaging Scanner (Bioscan, Inc., Washington, D.C.). The percent of recovered radiolabel converted to product was calculated, from which enzyme activity was determined. All incubations were conducted such that no more than 12% of the substrate (testosterone) was consumed.

The experimentally obtained data was computer fitted to a linear function by plotting the reciprocal of the enzyme activity (1/velocity) against the variable inhibitor concentration (Dixon, M. (1953), *Biochem. J.*, 55, 170). Assuming that the steroidal inhibitor is a competitive inhibitor against testosterone, a value for the inhibition constant ($K_i$) can be calculated from equation 1:

$$K_i=(B/A)/(S/K_m+1)S/K_m+1)$$  Equation 1 where B is the intercept on the 1/velocity axis, A is the slope of the line, S is the concentration of substrate (testosterone) used in the experiment, and $K_m$ is the Michaelis-Menton constant of the substrate (testosterone) determined in a separate experiment to be 4.5 μM.

Table II displays the results of the above testing and shows that the tested compounds of the invention are potent inhibitors of human steroid 5-α-reductase.

TABLE II

| Inhibition Constants of Human Prostatic Steroid 5-α-Reductase | |
|---|---|
| Compound | $K_i$ (nM) |
| (structure) | 5000 |

TABLE II-continued

Inhibition Constants of Human Prostatic Steroid 5-α-Reductase

| Compound | $K_i$ (nM) |
|---|---|
| [steroid with C17 CH(CH3)CH2OH, 4-F, 3-carboxylic acid] | 2000 |
| [steroid with 3-carboxylic acid, 4-ene] | 30 |
| [steroid with 17β-CON(iPr)2, 3,5-diene-3-carboxylic acid] | 7 |
| [steroid with 17α-CON(iPr)2, 3,5-diene-3-carboxylic acid ethyl ester] | 4000 |
| [steroid with 2,4-diene-3-carboxylic acid, 17β-N(iPr)2 formamide] | 52 |
| [steroid with 17β-CON(iPr)2, 4-F, 3-carboxylic acid] | 26 |
| [steroid with 17α-CON(iPr)2, 3-ene-3-carboxylic acid] | 85 |
| [3α-carboxy-5α-steroid with 17β-N(iPr)2 formamide] | 2200 |
| [steroid with 17β-NHC(O)C(CH3)3, 3,5-diene-3-carboxylic acid] | 30 |
| [steroid with 17β-N(iPr)2 formamide, 1,3,5-triene-3-carboxylic acid] | 50 |

TABLE II-continued

Inhibition Constants of Human Prostatic Steroid 5-α-Reductase

| Compound | $K_i$ (nM) |
|---|---|
| (6-fluoro Δ3,5-diene N,N-diisopropyl carboxamide steroid) | 32 |
| (Δ3,5-diene N,N-diisopropyl carboxamide steroid) | 50 |
| (5α-H Δ1,3-diene N,N-diisopropyl carboxamide steroid) | 62 |
| (Δ3,5-diene N,N-diisopropyl carboxamide steroid, variant) | 110 |
| (6-trifluoromethyl Δ3,5-diene N,N-diisopropyl carboxamide steroid) | 900 |
| (4-methyl Δ3,5-diene N,N-diisopropyl carboxamide steroid) | 35 |
| (17-ethynyl Δ3,5-diene carboxylic acid steroid) | 790 |
| (6-methyl Δ3,5-diene N,N-diisopropyl carboxamide steroid) | 170 |
| (5α-H Δ3-ene N-t-butyl carboxamide steroid) | 110 |

Certain compounds of the invention also were tested for their in vivo potency in inhibiting steroid 5-α-reductase activity. Male Charles River CD rats, 48 days old, weighing approximately 200 gm were administered 10 mg/kg of N,N-diisopropyl androst-3,5-diene-17β-carboxamide-3-carboxylic acid dissolved in propylene glycol and diluted in normal saline. Following compound administration the animals were sacrificed, the ventral prostates were excised, and DHT levels were measured by the following procedure.

Prostate tissue was excised, trimmed, weighed, minced and washed with phosphate buffer. The tissue then was homogenized in phosphate buffer and extracted by addition of ethyl acetate and mixing on an orbital mixer for forty-five minutes. The ethyl acetate was evaporated, the residue was reconstituted in ethanol, and was centrifuge filtered using 0.45 μM filter paper. The components then were separated using reverse-phase HPLC collecting the DHT fraction. The fraction was reduced to dryness and reconstituted in standard DHT assay buffer available from Amersham. DHT levels then were measured using standard techniques such as radioimmunoassay.

In the compound treated rats, prostatic DHT levels were decreased forty percent relative to vehicle-treated controls four hours after compound administration. The decreased DHT levels were maintained for greater than eight hours after administration, and had returned to control levels twenty four hours after treatment. A single 10 mg/kg dose of the methyl ester of the above compound decreased prostatic DHT levels forty eight percent relative to vehicle-treated controls after six hours. Thus, even though this compound does not inhibit steroid-5-α-reductase in vitro, in vivo administration of this compound produces significant enzyme inhibition.

N,N diisopropyl-androst-3,5 diene 17β-carboxamide-3-carboxylic acid also was tested for its effects on prostatic growth. Twice daily oral administration for fourteen days of 0.5 to 50 mg/kg of this compound to immature rats produced a dose dependent decrease in prostatic growth. Prostrate weights from animals in the maximum dose group were forty to fifty percent less than controls.

Using procedures similar to those described above the in vivo effects of 17β-N-t-butylcarbox-amide-androst-3,5-diene-3-carboxylic acid also were studied. Rats received a single oral dose of vehicle or 5, 10, 20 or 50 mg/kg of this compound. At all doses, prostate dihydrotestosterone levels were significantly reduced to approximately fifty percent of controls while testosterone levels remained unaffected.

Rats also were given 10 mg/kg of this compound and prostate testosterone and dihydrotestosterone levels at several points over twenty four hours. Dihydrotestosterone levels were significanly depressed to approximately sixty percent of controls at all time points from two to eighteen hours after treatment, and returned to control values by twenty-four hours post treatment. Prostate testosterone levels were viable without consistent trends.

Additionally, rats were given this compound at 1, 5, 10, 25 or 50 mg/kg twice daily for two weeks to determine if repeated treatment caused a reduction in ventral prostate weight. Ventral prostate weight was ninety percent of control at 5 mg/kg dose level and sixty five percent of control at the 10 and 50 mg/kg dose level Seminal vescicle weights were significantly reduced at all treatment levels.

The pharmaceutically active compounds of the present invention are incorporated into convenient dosage forms such as capsules, tablets, or injectable preparations. Solid or liquid pharmaceutical carriers are employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid such as an ampoule, or an aqueous or nonaqueous liquid suspension.

The pharmaceutical preparations are made following conventional techniques of a pharmaceutical chemist involving mixing, granulating, and compressing, when necessary, for tablet forms, or mixing, filling and dissolving the ingredients, as appropriate, to give the desired oral or parenteral products.

Doses of the presently invented pharmaceutically active compounds in a pharmaceutical dosage unit as described above will be an efficacious, nontoxic quantity selected from the range of 0.1–1,000 mg/kg of active compound, preferably 1–100 mg/kg. The selected dose is administered to a human patient in need of steroid 5-α-reductase inhibition from 1 6 times daily, topically, orally, rectally, by injection, or continuously by infusion. Oral dosage units for human administration preferably contain from 1 to 500 mg of active compound. Parenteral administration, which uses lower dosages is preferred. Oral administration, at higher dosages, however, also can be used when safe and convenient for the patient.

The method of this invention of inhibiting steroid 5-α-reductase activity in mammals, including humans, comprises administering to a subject in need of such inhibition an effective steroid 5-α-reductase inhibiting amount of a compound of Formula (III) in which $R^1=H$.

Contemplated equivalents of Formula I compounds are compounds otherwise corresponding thereto wherein substituents have been added to any of the unsubstituted positions of the Formula (III) compounds or the methyl group at C-13 is absent or replaced by $C_{1-4}$alkyl provided such compounds have the pharmaceutical utility of Formula (III) compounds.

The following examples illustrate preparation of Formula (III) compounds and pharmaceutical compositions containing these compounds. The examples are not intended to limit the scope of the invention as defined hereinabove and as claimed below.

EXAMPLE 1

20-α-(Hydroxymethyl)-5-α-pregn-3-ene-3-carboxylic acid (i) 20-α-(Hydroxymethyl)-pregn-4-ene-3-one Pregn-4-ene-3-one-20-α-carboxaldehyde (16.4 g, 50 mmol) in ethanol (250 ml) and THF (50 ml) was cooled to 0° C. and a solution of sodium borohydride (NaBH$_4$) in 125 ml ethanol was added dropwise. The reaction mixture was stirred overnight at 25° C. Acetic acid was added to the reaction mixture until neutral pH and then the solution was evaporated to remove excess ethanol. The residue was dissolved in trichloromethane and washed with saturated sodium bicarbonate solution, water and brine. The organic layer was then dried over sodium sulfate and evaporated to dryness to yield 13.9 g (82%) of 20-α-(hydroxymethyl)pregn-4-ene-3-one.

(ii) 20-α-(t-Butyldimethylsilyloxymethyl)pregn-4-ene-3-one

A solution of 20-α-(hydroxymethyl)pregn-4-ene-3-one (1.2 g, 3.5 mmol), t butyldimethylsilyl chloride (627 mg, 4.15 mmol) and imidazole (287 mg, 4.22 mmol) in DMF (40 ml) was stirred overnight at 40° C. The reaction mixture was then poured into ice water and the emulsion was washed three times with ethyl acetate. The organic layers were combined, washed with cold dilute hydrochloric acid, water and brine; dried over sodium sulfate and evaporated to dryness. Recrystallization from methanol afforded 1.1 g (70%) of 20-α-(t-butyldimethylsilyloxymethyl)pregn-4-ene-3-one.

(iii) 20-α-(t-Butyldimethylsiloxymethyl)-3-(trifluoromethylsulfonate) -5-α-pregn-3-ene Ammonia (200 ml) was double distilled into a 3 neck roundbottom flask equipped with a dry ice condenser and argon bubbler. Lithium (Li) wire (120 mg, 17.4 mmol) was dissolved in ammonia (NH₃). A solution of 20-α-(t-butyldimethylsiloxymethyl)-pregn-4-ene-3-one 3-one (3 g. 6.76 mmol) and aniline (49.5 1, 5.4 mmol) in THF (50 ml) was added dropwise to the Li/NH₃ solution. The reaction mixture was stirred at −78° C. for 15 minutes and then quenched with isoprene until the blue color disappeared. The volatiles were slowly evaporated (to avoid excess foaming) by slow warming, and eventually at 0.5 mmHg for 1 and ½ hours. The residue was redissolved in THF (50 ml) and cooled to 0° C. A solution of N phenyltrifluoromethylsulfonimide (7 g, 20 mmol) in THF (10 ml) was added to the reaction mixture, and stirring was continued overnight at 4° C. The solvent was then evaporated and the residue was chromatographed on silica gel eluting with 3% ethyl acetate in hexane to yield 2.24 g (57%) of the 20-α-(t-butyl-dimethyl-siloxymethyl)-3-(trifluoromethylsulfonate)-5-α-pregn -3-ene.

(iv) 20-α-(t-Butyldimethylsiloxymethyl)-3-carbomethoxy-5-α-pregn-3-ene

20-α-(t-Butyldimethylsiloxymethyl)-3-(trifluoromethylsulfonate) -5-α-pregn-3-ene (100 mg, 0.173 mmol) was dissolved in methanol (0.5 ml) and DMF (1 ml). Triethylamine (55 μl, 0.386 mmol), triphenyl-phosphine (9 mg, 0.034 mmol) and palladium(II) acetate (3.8 g, 0.017 mmol) were then added to the solution and CO was bubbled through the solution for 5 minutes. The reaction mixture was then stirred overnight at 45° C. under 1 atmosphere of CO, diluted with ethyl acetate and washed with water until neutral pH. The organic layer was dried over sodium sulfate and evaporated. The dark oil was purified by chromatography on silica gel eluting with 10% ethyl acetate in hexane to yield 52 mg (61%) of the desired product; 20-α-(t-Butyldimethylsiloxymethyl)-3-carbomethoxy-5-α-pregn-3-ene.

(v) 20-α-(Hydroxymethyl)-3-carbomethoxy-5-α-pregn-3-ene

20-α-(t-Butyldimethylsiloxymethyl)-3-carbomethoxy-5-α-pregn 3 ene (500 mg, 1.05 mmol) was dissolved in THF (20 ml) and 2 ml of a 1 molar solution of tetrabutylammonium fluoride in THF was added. The reaction mixture was stirred at room temperature for 3.5 hours and then diluted with water. The aqueous mixture was washed thoroughly with dichloromethane. The organic layers were combined, dried over sodium sulfate and evaporated to dryness. Purification by flash chromatography eluting with 20% ethyl acetate in hexane afforded 300 mg (78%) of 20-α-hydroxymethyl-3-carbomethoxy-5-α-pregn-3-ene.

(vi) 20-α-(Hydroxymethyl)-5-α-pregn-3-ene-3-carboxylic acid

20-α-(Hydroxymethyl)-3-carbomethoxy-5-α-pregn-3-ene (300 mg, 0.802 mmol) was dissolved in THF (15 ml) and methanol (15 ml). Lithium hydroxide (8 ml of a 1 N aqueous solution) was added and the reaction mixture was stirred overnight. The reaction mixture was then diluted with water and evaporated to remove excess methanol and THF. The aqueous solution was acidified with 5% hydrochloric acid and washed several times with ethyl acetate. The organic layers were combined, washed with brine, dried over sodium sulfate, and evaporated to dryness. Recrystallization from ethyl acetate and hexane afforded 242 mg (84%) of the desired acid; 20-α-(hydroxymethyl)-5-α-pregn-3-ene-3-carboxylic acid, m.p. 197–203° C.

EXAMPLE 2

N,N-Diisopropyl-5-α-androst-3-ene-17β-carboxamide-3-carboxylic acid (i) 17β-(Hydroxymethyl)-androst-4-ene-3-ol Approximately 750 ml of dry THF was added to a 3-neck round bottom flask equipped with a condenser, argon bubbler and mechanical stirrer. The flask was cooled to 0° C. and lithium aluminum hydride (LAH) (11.39 g, 0.3 mol) was slowly added. After all of the LAH was added, the flask was warmed to room temperature. A solution of methyl androst-4-ene-3-one-17β-carboxylate (66 g, 0.2 mol) in 600 ml of THF was very slowly added to the LAH slurry. After the addition of the steroid, the reaction mixture was slowly warmed to reflux. After 2 hours the excess LAH was quenched with 11.4 ml water, 11.4 ml 15% sodium hydroxide (NaOH) and 2B ml water. The salts were removed by filtration and washed with approximately 1 liter of warm THF. Concentration of the combined organic solutions afforded 63 g (94%) of 17β-(hydroxymethyl)-androst-4-ene-3-ol as mixture of α and β isomers.

(ii) 3-Oxo-17β-(hydroxymethyl)-4-androstene

A solution of 17β-(hydroxymethyl) -androst-4-ene 3 ol (27 g, 0.089 mol) in 1200 ml trichloromethane was treated with activated manganese dioxide (66 g). After 3 hours the mixture was filtered. Concentration afforded 26 g (96%) of 3-oxo-17β-(hydroxymethyl)-4 androstene (m.p. 151° C.).

(iii) 3-Oxo-17β-(t-butyldimethylsilyloxymethyl) -4-androstene

To a solution of 3-oxo-17β-(hydroxymethyl) 4 androstene (15 g, 0.05 mol) in 200 ml DMF was added 5.8 g (0.085 mol) imidazole followed by 9.7 g (0.065 mol) t-butyldimethylsilyl chloride. The reaction mixture was stirred at room temperature under argon, for 2.5 hours. The reaction mixture was then poured into 250 ml ice water and washed 3 times with ethyl acetate. The combined organic layers were washed twice with cold 5% hydrochloric acid and once each with saturated sodium bicarbonate solution and brine. The organic layer was dried over sodium sulfate and evaporated. Recrystallization from methanol afforded 16.9 g (82%) of 3-oxo- 17β-(t-butyldimethylsilyloxymethyl) -4-androstene as a white crystalline solid.

(iv) 17β-(t-Butyldimethylsilyloxymethyl)-3-(trifluoromethylsulfonate)-5-α-androst-3-ene Ammonia (300 ml) was double distilled into a 3 neck round bottom flask equipped with a dry ice condenser and argon bubbler. Li wire, 250 mg (3 eq), was dissolved in the ammonia and stirred for 15 minutes to ensure dryness. Freshly distilled aniline, 0.53 ml (0.8 eq), was then added. A solution of 3 g (7.2 mmol) of 3-oxo-17β-(t-butyldimethylsilyloxymethyl)-4-androstene in 50 ml of dry THF was added dropwise to the Li/NH₃ solution. An additional 50 ml dry THF was added to aid in solubility. The reaction mixture was stirred at −78° C. for 2 hours and then quenched with isoprene until the blue color disappeared. The volatiles were slowly evaporated (to avoid excess foaming) by slow warming, and eventually at 0.5 mmHg for 1.5 hours. The oily residue was redissolved in dry THF (100 ml) and cooled to 0° C. A solution of 7.7 g (3 eq) of N phenyltrifluoromethylsulfonimide in 50 ml THF was added, the flask was tightly sealed, and stirred overnight at 4° C. The mixture was then concentrated to dryness, and chromatographed on silica eluting with hexane. Recrystallization from ethyl acetate yielded 2.5 g (63%) of 17β-(t-butyldimethylsilyloxymethyl) -3-(trifluoromethylsulfonate)-5-α-androst-3--ene (m.p. 120–121° C.).

(v) Methyl 17β-(t-butyldimethylsilyloxymethyl)-5-α-androst-3-ene-3-carboxylate

To a solution of 3 g (5.46 mmol) of 17β-(t-butyldimethylsilyloxymethyl)-3-(trifluoromethylsulfonate) -5-α-androst-3-ene in 10 ml DMF and 10 ml methanol was added 1.5 ml (2 eq) triethylamine and 123 mg (0.03 eq) of the catalyst bis(triphenylphosphine) palladium(II) acetate. Carbon monoxide (CO) was bubbled through the solution for 5 minutes and the reaction mixture was then stirred at room temperature overnight under 1 atmosphere of CO. The mixture was diluted with ethyl acetate and washed with water until neutral pH. The organic layer was dried over sodium sulfate and evaporated. Chromatography on silica gel eluting successively with 5%, 10%, and 20% ethyl acetate in hexane followed by recrystallization from methanol afforded methyl 17β-(t-butyldimethylsilyloxymethyl)-5-α-androst-3-ene-3-carboxylate.

(vi) 3-Carbomethoxy-3-androstene-17β-carboxylic acid

Methyl 17β-(t-butyldimethylsilyloxymethyl) -5α-androst-3-ene-3-carboxylate (500 mg), was dissolved in 150 ml acetone. Jones reagent was added until a red color persisted. Isopropanol was then added to quench excess Jones reagent. The acetone was decanted off and the residual chromium salts were then dissolved in water and washed 3 times with dichloromethane. The organic layers were combined and passed through a plug of florosil and concentrated to give 360 mg (99%) of 3-carbomethoxy-3-androstene-17β-carboxylic acid.

(vii) 3-Carbomethoxy-3-androstene-17β-N,N -diisopropylcarboxamide

3-Carbomethoxy-3-androstene-17β-carboxylic acid, (360 mg, 0.78 mmol) was suspended in 10 ml of dry toluene and treated with 0.4 ml of oxalyl chloride for 2 hours under argon. The reaction mixture was then evaporated ( 1 mm Hg) and the residue was dissolved in 10 ml dry THF. A solution of 0.6 ml diisopropylamine in 2 ml dry THF was added and the reaction mixture stirred for 1 hour. The mixture was diluted with ice water and extracted with dichlorome thane. The organic layer was then washed twice with cold 5% hydrochloric acid, sodium hydroxide and brine; dried over sodium sulfate and evaporated. Chromatography on silica gel eluting with 20% ethyl acetate in hexane followed by recrystallization from diethyl ether afforded 3-carbomethoxy-3-androstene 178 N,N -diisopropylcarboxamide.

(viii) N,N-Diisopropyl-5-α-androst-3-ene-17β-carboxamide-3-carboxylic acid

3-Carbomethoxy-3-androstene-17β-N,N -diisopropylcarboxamide (300 mg, 0.7 mmol) and 300 mg of K₂CO₃ were added to 20 ml of 10:1 methanol:water solution and refluxed under argon for 20 hours. The mixture was then concentrated to dryness and dilute with water. The aqueous layer was rinsed with ethyl acetate and acidified. The emulsion was washed several times with dichloromethane. The organic layer was dried over sodium sulfate and evaporated. The product was recrystallized by dissolving in ethyl ether, adding ethyl acetate and concentration to afford N,N diisopropyl 5-α-androst-3-ene 17β-carboxamide 3-carboxylic acid, m.p. 159–162° C.

EXAMPLE 3

N,N-Diisopropyl-androst-3,5-diene-17β-carboxamide-3-carboxylic acid (i) Androst-4-ene-3-one-17β-carboxylic acid Methyl androst-4-ene-3-one-17β-carboxylate (20 g, 60 mmol) was dissolved in 700 ml of a 20:1 solution of methanol:water and potassium hydroxide (7 g) was added and the solution was refluxed under argon for 24 hours. The reaction mixture was then acidified with 5% hydrochloric acid and 250 ml water was added. After aging for 1 hour, the mixture was filtered and dried to yield 18 g (94%) of androst-4-ene-3-one-17β-carboxylic acid as a white crystalline solid.

(ii) Androst-4-ene-3-one-17β-N,N-diisopropylcarboxamide

A solution of androst-4-ene-3-one-17β-carboxylic acid (18 g, 0.06 mol) in 350 ml of toluene was azeotropically dried until approximately 100 ml distillate was collected. The solution was then cooled to 10° C. Pyridine (6.7 ml, 0.08 mol) was added, followed by slow addition of a solution of oxalyl chloride (7.2 ml, 0.08 mol) in 10 ml of toluene. The reaction mixture was stirred at room temperature (under argon) for 2 hours, and then cooled to 0° C. A solution of diisopropylamine (89 ml, 0.6 mol) in 40 ml toluene was added dropwise such that the temperature did not exceed 40° C. The reaction mixture was stirred for 1 hour and then quenched with 300 ml ice water. The layers were separated and the aqueous layer was extracted 4 times with ethyl acetate (800 ml). The organic layers were combined and washed with 5% hydrochloric acid and brine. The organic layer was then dried over sodium sulfate and concentrated to dryness. Recrystallization by dissolving in 10 ml toluene and adding 200 ml hexane afforded 16.5 g (69%) of androst-4-ene-3-one-17β-N,N-diisopropylcarboxamide (m.p. 236–239° C.).

(iii) 17β-(N,N-Diisopropylcarboxamide)-3-(trifluoromethylsulfonate)-androst -3,5-diene Androst-4-ene-3-one-17β-N,N -diisopropylcarboxamide (5 g, 12.5 mmol) was dissolved into 50 ml of methylene chloride. 2,6-Di-t-butyl-4-methylpyridine (3.08 g, 17.0 mmol) was then added to the steroid solution and stirred at room temperature for 15 minutes. Trifluoromethane sulfonic anhydride (3.5 ml, 19 mmol)

was added to the solution and stirring continued for 30 minutes. The reaction mixture was then diluted with 50 ml methylene chloride and filtered. The organic layer was washed twice with 5% hydrochloric acid, saturated sodium bicarbonate, and brine. It was then dried over sodium sulfate and evaporated. The triflate was purified by chromatography on silica gel eluting with 20% ethyl acetate in hexane to yield 4 g (61%) of 17β-(N,N-diisopropylcarboxamide)-3-(trifluoromethylsulfonate)-androst-3,5-diene.

(iv) 3-Carbomethoxy-androst-3,5-diene-17β-N,N -diisopropylcarboxamide

To a solution of 17β-(N,N -diisopropylcarboxamide)-3-(trifluoromethylsulfonate)androst-3,5-diene (4 g, 7.5 mmol) in 60 ml of a 1:1 solution of methanol in DMF was added bis(triphenylphosphine)palladium(II) acetate (570 mg) and a large excess (20 ml) of triethylamine. Carbon monoxide was bubbled through the solution for 5 minutes and the reaction was stirred at 65° C. overnight under 1 atmosphere of CO. The mixture was then diluted with ethyl acetate and washed with water until neutral pH. The organic layer was dried over sodium sulfate and evaporated to a brown oil. Purification by chromatography on silica gel eluting with 20% ethyl acetate in hexane, followed by recrystallization from ethyl ether and hexane afforded 2.1 g (64%) of 3-carbomethoxy-androst-3,5-diene-17β-N,N -diisopropylcarboxamide, m.p. 159-162° C.

(v) N,N-Diisopropyl-androst-3,5-diene-17β-carboxamide-3-carboxylic acid

3-Carbomethoxy-androst-3,5-diene-17β-N,N-diisopropylcarboxamide (1.4 g, 3.17 mmol) and 1 g of K$_2$CO$_3$ were added to 88 ml of a 10:1 solution of methanol-water and refluxed under argon for 20 hours. The mixture was then concentrated to dryness and diluted with water. The aqueous layer was rinsed with ethyl acetate and acidified. The emulsion was washed several times with dichloromethane. The organic layer was dried over sodium sulfate and evaporated. The product was recrystallized by dissolving in ethyl ether, adding ethyl acetate and concentration to afford N,N-diisopropyl-androst-3,5-diene-17β-carboxamide-3-carboxylic acid (m.p. 230-234° C.).

EXAMPLE 4

17β-(N,N-Diisopropylcarboxamide)-4-fluoro-5-α-androst-3-ene-3-carboxylic acid (i) 3-Oxo-17β-(hydroxymethyl)-5-α-androstane Ammonia (500 ml) was distilled into a 3-neck round-bottom flask equipped with a dry ice condenser and argon bubbler. Li wire (3 g) was dissolved in the ammonia and stirred for 15 minutes to ensure dryness. A solution of 3-oxo 17β-(hydroxymethyl)-4-androstene (prepared as described in Example 2 (ii), 37.5 g, 0.123 mol) in 625 ml THF and t-butyl alcohol (6.25 ml, 5 0.8 eq) was added dropwise to the Li/NH$_3$ solution. The reaction was stirred at −78° C. for 2 hours and quenched with isoprene until the blue color disappeared. The resulting enolate was then quenched with ammonium chloride and the ammonia was allowed to evaporate. Acetone was added to the residue and gently refluxed. The acetone solution was then filtered and evaporated to dryness to yield 24.7 g (79%) of 3-oxo-17β-(hydroxymethyl)-5-α-androstane.

(ii) 3-Oxo-5-α-androstane-17β-carboxylic acid

The title compound was prepared according to Example 2 (vi) by replacing 3-oxo-17β-(hydroxymethyl) 5-α-androstane for methyl 17β-(t -butyldimethylsilyloxymethyl)-5-α-androst-3-ene-3-carboxylate.

(iii) 3-Oxo-5-α-androstane-17β-N,N-diisopropylcarboxamide

3-Oxo-5-α-androstane-17β-carboxylic acid was suspended in toluene (100 ml) and an excess of oxalyl chloride (8 ml) was added. The reaction mixture was stirred for 1 hour at 25° C. (under argon). The volatiles were then removed (0.5 mmHg for 2 hours). The residue was resuspended in THF (25 ml), cooled to 0° C., and diisopropyl amine (10 ml) was added. The reaction mixture was stirred at 0° C. for 2 hours and then diluted with water. The aqueous mixture was extracted with ethyl acetate and evaporated. Purification by chromatography on silica gel eluting with 20% ethyl acetate in hexane afforded 3.15 g (78%) of 3-oxo-5-α-androstane-17β-N,N -diisopropylcarboxamide.

(iv) 3-Oxo-5-α-androst-1-ene-17β-N,N-diisopropylcarboxamide

To a solution of 3-oxo-5-α-androstane-17β-N,N diisopropylcarboxamide (2.3 g, 5.74 mmol) in 100 ml ethyl acetate was added phenylselenyl chloride (1.1 g, 5.74 mmol) and the reaction mixture was stirred for 2 hours. The reaction mixture was then washed with 5% sodium bicarbonate solution and brine. The ethyl acetate solution was cooled to 0° C. and 50 ml THF was added. Hydrogen peroxide (6 ml of a 30% solution) was slowly added and the reaction mixture stirred for 2 hours. The reaction mixture was then washed with 5% sodium bicarbonate solution, brine and evaporated to dryness. Purification by chromatography on silica gel eluting with 20% ethyl acetate in hexane afforded 1.3 g (56.5%) of 3-oxo-5-α-androst-1-ene-17β-N,N-diisopropylcarboxamide.

(v) 3-Oxo-5-α-androstane-1,2-alpha-epoxide-17β-N,N-diisopropylcarboxamide

3-Oxo-5-α-androst-1-ene-17β-N,N -diisopropylcarboxamide (4.6 g, 11.5 mmol) was dissolved in 50 ml methanol and cooled to 15° C. To the solution was added hydrogen peroxide (0.8 ml of a 30% solution) followed by sodium hydroxide (0.16 ml of a 10% solution) in 2 ml methanol. The ice bath was removed and stirring was continued at room temperature for 1 hour. The reaction mixture was then poured into ice water and washed twice with dichloromethane. The organic layers were combined and washed with water and brine; dried over sodium sulfate and evaporated. Trituration in acetone afforded 4.0 g (83.7%) of the desired epoxide; 3-oxo-5-α-androstane-1,2-α-epoxide-17β-N,N -diisopropylcarboxamide.

(vi) 3-Oxo-4-fluoro-5-α-androst-1-ene-17β-N,N-diisopropylcarboxamide

3-Oxo-5-α-androstane-1,2-α-epoxide-17β-N,N-diisopropylcarboxamide (1.7 g, 4 mmol) was dissolved in 25 ml THF and cooled to −20° C. Pyridinium poly(hydrogen fluoride) (10 ml) was slowly added to the solution (under argon). The reaction mixture was warmed to 0° C., stirred 30 minutes then warmed to room temperature and stirred for 15 minutes. The reaction mixture was poured into ice water and washed with ethyl acetate. The organic layer was washed with water, 5% sodium bicarbonate solution and brine; dried over sodium sulfate and evaporated. Purification by chromatography on silica gel eluting with 20% ethyl acetate in hexane yielded 750 mg (44%) of the desired 3-oxo-4-fluoro-5-α-androst-1-ene-17β-N,N-diisopropylcarboxamide.

(vii) 17β-(N,N-Diisopropylcarboxamide)-3-(trifluoromethylsulfonate)-4-fluoro-5-α-androst-1,3-diene A solution of lithium bis(trimethylsilyl)amide (4.2 mmol, 2.2 eq) in 2 ml THF was cooled to −78° C. A solution of 3-oxo-4-fluoro-5-α-androst-1-ene -17β-N,N-diisopropylcarboxamide (800 mg, 1.9 mmol) in 10 ml THF was added and the reaction mixture was stirred for 1 hour. A solution of N phenyltrifluoromethanesulfonimide (857 mg, 2.4 mmol) in 8 ml THF was then added and the reaction mixture was stirred for 1.5 hours at −78° C. The reaction mixture was then evaporated to dryness and chromatographed on silica gel eluting with 20% ethyl acetate in hexane. Trituration in a hexane and ether solution afforded 460 mg (46%) of the desired product, 17β-(N,N-diisopropylcarboxamide) 3-(trifluoromethylsulfonate) -4-fluoro-5-α-androst-1,3-diene.

(viii) 3-Carbomethoxy-4-fluoro-5-α-androst-1,3-diene-17β-N,N-diisopropylcarboxamide The title compound was prepared according to Example 1 (iv) by substituting 17β-(N,N -diisopropylcarboxamide)-3-(trifluoromethylsulfonate)-4-fluoro-5-α-androst-1,3-diene for 20-α-(t-butyldimethylsilyloxymethyl)-3-(trifluoromethylsulfonate)-5-α-pregn-3-ene.

(ix) 3-Carbomethoxy-4-fluoro-5-α-androst-3-ene-17β-N,N-diisopropylcarboxamide

3-Carbomethoxy-4-fluoro-5-α-androst-1,3-diene-17β-N,N-diisopropylcarboxamide (120 mg, 0.26 mmol) in 15 ml of a 2:1 solution of ethyl acetate and hexane was hydrogenated at 25° C. and 1 atmosphere over 20 mg 10% palladium on carbon. The solution was filtered to remove the catalyst and concentrated to a white solid (120 mg). Recrystallization from methanol and acetone afforded 55 mg (46%) of the desired 3 carbomethoxy 4-fluoro-5-α-androst 3-ene 17β-N,N diisopropylcarboxamide, m.p. 171-172° C.

(x) 17β-(N,N-Diisopropylcarboxamide)-4-fluoro-5-α-androst-3-ene-3-carboxylic acid The title compound was prepared according to Example 2 (viii) by substituting 3-carbomethoxy-4-fluoro-5-α-androst-3-ene-17β-diisopropylcarboxamide for 3-carbomethoxy-5-α-androst-3-ene 17β-N,N-diisopropylcarboxamide.

EXAMPLE 5

20-α-(Hydroxymethyl)-4-fluoro-5-α-pregn-3-ene-3-carboxylic acid (i) 20-α-(Hydroxymethyl)-5-α-pregnan-3-one The title compound was prepared according to Example 4 (i) by substituting 20-α -(hydroxymethyl)-pregn-4-ene-3-one for 3-oxo-17β-(hydroxymethyl)-4-androsten.

(ii) 20-α-(Hydroxymethyl)-5-α-pregn-1-ene-3-one

The title compound was prepared according to Example 4 (iv) by substituting 20-α-(hydroxymethyl) 5-α-pregnane 3 one for 3 oxo 5-α-androstane 17β-N,N diisopropylcarboxamide.

(iii) 20-α-(Hydroxymethyl)-1,2-α-epoxide -5-α-pregnan-3-one

The title compound was prepared according to Example 4 (v) by substituting 20-α-(hydroxymethyl)-5-α-pregn-1-ene-3-one for 3-oxo-5-α-androst-1-ene-17β-N,N-diisopropylcarboxamide.

(iv) 20-α-(Hydroxymethyl)-4-fluoro-5-α-pregn-1-ene-3-one

The title compound was prepared according to Example 4 (vi) by substituting 20-α-(hydroxymethyl) 1,2-α-epoxide 5-α-pregnane 3 one for 3-oxo-1,2-α-epoxide-5-α-androstane-17β-N,N-diisopropylcarboxamide.

(v) 20-α-(t-Butyldimethylsilyloxymethyl) -4-fluoro-5-α-pregn-1-ene-3-one

The title compound was prepared according to Example 1 (ii) by substituting 20-α-(hydroxymethyl) 4 fluoro 5 -α-pregn 1-ene 3 one for 20-α-(hydroxymethyl) pregn-4-ene 3 one.

(vi) 20-α-(t-Butyldimethylsilyloxymethyl) -4-fluoro-3-(trifluoromethylsulfonate)-5-α-pregn-1,3-diene The title compound was prepared according to Example 4 (vii) by substituting 20-α-(t -butyldimethylsilyloxymethyl) 4-fluoro 5-α-pregn 1 ene -3-one for 3-oxo 4 fluoro 5 -α-androst-1-ene-17β-N,N -diisopropylcarboxamide.

(vii) 3 Carbomethoxy-20 -α-(t-butyldimethylsilyloxymethyl) -4-fluoro-5-α-pregn -1,3 diene The title compound was prepared according to Example 4 (viii) by substituting 20 -α-(t-butyldimethylsilyoxymethyl) -4-fluoro 3 (trifluoromethylsulfonate) -5α-pregn 1,3 diene for 17β-(N,N -diisopropylcarboxamide) 3 (trifluoromethylsulfonate) 4-fluoro-5-α-androst 1,3 diene.

(viii) 3 Carbomethoxy 20-α-(t-butyldimethylsilyloxymethyl) -4fluoro 5 -α-pregn-3-ene The title compound was prepared according to Example 4 (ix) by substituting 3-carbomethoxy -20-α-(t-butyldimethylsilyloxymethyl)-4-fluoro 5-α-pregn 1,3 diene for 3 carbomethoxy-4 fluoro 5-α-androst 1,3-diene-17β-N,N-diisopropylca-rboxamide.

(ix) 3-Carbomethoxy-20-α-(hydroxymethyl)-4-fluoro-5-α-pregn-3-ene

To a solution of 3-carbomethoxy 20-α-(t-butyldimethylsilyloxymethyl) 4-fluoro 5-α-pregn-3 ene (610 mg, 1.2 mmol) in THF 20 ml was added 2.4 mmol tetrabutylammonium fluoride and the reaction mixture was stirred at 25° C. for 3.5 hours under argon. The reaction mixture was then poured into ether and washed with water and brine; dried over sodium sulfate and evaporated. Chromatography on silica gel eluting with 15% ethyl acetate in hexane yielded 200 mg (43%) of the desired 3 carbomethoxy 20-α-(hydroxymethyl) 4 fluoro 5-α-pregn 3-ene, m.p. 177° C.

(x) 20-α-(Hydroxymethyl)-4-fluoro-5-α-pregn-3-ene-3-carboxylic acid

The title compound (m.p. 233-236° C. from methanol:acetone) was prepared according to Example 1 (vi) by substituting 3-carbomethoxy-20-α-(hydroxymethyl)- 4-fluoro-5-α-pregn-3-ene for 20-α-(hydroxymethyl)-3-carbomethoxy-5-α-pregn-3-ene.

EXAMPLE 6

17β-N,N-Diisopropylcarboxamide-5-α-androst-1,3-diene-3-carboxylic acid (i) 17β-(N,N-Diisopropylcarboxamide)-3-(trifluoromethylsulfonate)-5-α-androst-1,3-diene The title compound was prepared according to Example 4 (vii) by substituting 3-oxo-5-α-androst-1-ene-17β-N,N-diisopropylcarboxamide for 3-oxo-4-fluoro-5-α-androst-1-ene-17β-N,N-diisopropylcarboxamide.

(ii) 3-Carbomethoxy-5-α-androst-1,3-diene-17β-N,N-diisopropylcarboxamide

The title compound (m.p. 174°176° C.) was prepared according to Example 1 (iv) by substituting 17β-(N,N-diisopropylcarboxamide)-3-(trifluoromethylsulfonate)-5-α-pregn-3-ene.

(iii) 17β-N,N-Diisopropylcarboxamide-5-α-androst-1,3-diene-3-carboxylic acid

The title compound (m.p. 163° C.) was prepared according to Example 2 (viii) by substituting 3-carbomethoxy-5-α-androst-1,3-diene-17β-N,N-diisopropylcarboxamide for 3-carbomethoxy-5-α-androst-3-ene-17β-N,N-diisopropylcarboxamide.

EXAMPLE 7

5-α-Pregn-3-ene-(20R)-3,20-dicarboxylic acid (i) 3-Carbomethoxy-5-α-pregn-3-ene-(20R)-20-carboxylic acid To a solution of 20-α-(hydroxymethyl)-3-carbomethoxy-5-α-pregn-3-ene, prepared as in Example 1, (374 mg, 1.0 mmol) in 25 ml acetone is added Jones reagent dropwise until a red color persists. Isopropanol is then added to quench the excess oxidant. The solution is decanted from the gummy chromium salts, concentrated, and partioned between dichloromethane and water. The salts are dissolved in water and extracted with dichloromethane. The combined organic layers are then washed with brine, dried over sodium sulfate, and concentrated to yield 3-carbomethoxy-5-α-pregn-3-ene-(20R)-20-carboxylic acid.

(ii) 5-α-Pregn-3-ene-(20R)-3,20-dicarboxylic acid

The title compound is prepared according to Example 1 (vi) by substituting 3-carbomethoxy-5-α-pregn-3-ene-(20R)-20-carboxylic acid for 20-α-(hydroxymethyl)-3-carbomethoxy-5-α-pregn-3-ene.

EXAMPLE 8

N,N-Diisopropyl-5-α-pregn-3-ene-(20R)-20-carboxamide-3-carboxylic acid

The title compound was prepared according to Example 2 (vii–viii) by substituting 3-carbomethoxy-5-α-pregn-3-ene-(20R)-20-carboxylic acid, prepared as in Example 7, for 3-carbomethoxy-3-androstene-17β-carboxylic acid.

EXAMPLE 9

5-α-Androst-3-ene-17β-carboxaldehyde-3-carboxylic acid (i) 3-Carbomethoxy-5-α-androst-3-ene-17β-carboxychloride A solution of 3-carbomethoxy-3-androstene-17β-carboxylic acid (462 mg, 1.0 mmol) is suspended in 10 ml toluene and treated with 0.5 ml of oxalyl chloride for 2 hours. The volatile materials are then removed at 1 mmHg leaving a residue of 3-carbomethoxy-5-α-androst-3-ene-17β-carboxylchloride.

(ii) 3-Carbomethoxy-5-α-androst-3-ene-17β-carboxaldehyde

A solution of 3-carbomethoxy-5-α-androst-3-ene-17β-carboxylchloride (480 mg, 1.0 mmol) in 10 ml tetrahydrofuran is treated with lithium tri-t-butoxyaluminum hydride (254 mg, 1.0 mmol) at 0° C. for one hour to yield, after aqueous workup, 3-carbomethoxy-5-α-androst-3-ene-17β-carboxaldehyde.

(iii) 5-α-Androst-3-ene-17β-carboxaldehyde-3-carboxylic acid

The title compound is prepared according to Example 2 (viii) by substituting 3-carbomethoxy-5-α-androst-3-ene-17β-carboxaldehyde for 3-carbomethoxy-3-androstene-17β-N,N-diisopropylcarboxamide.

EXAMPLE 10

5-α-Androst-3-ene-17β-(1-oxobutyl)-3-carboxylic acid (i) 3-Carbomethoxy-17β-(1-oxobutyl)-5-α-androst-3-ene A solution of 3-carbomethoxy-5-α-androst-3-ene-17β-carboxylchloride (480 mg, 1 mmol), prepared as in Example 9, in 10 ml THF is treated with 1.0 mmol of di-n-butyl copperlithium at −κ° C. The reaction is quenched with aqueous ammonium chloride. Extraction with dichloromethane followed by concentration of the organic extracts and chromatography of the residue yields 3-carbomethoxy-17β-(1-oxobutyl)-5-α-androst-3-ene.

(ii) 5-α-Androst-3-ene-17β-(1-oxobutyl)-3-carboxylic acid

The title compound is prepared according to Example 1 (vi) by substituting 3-carbomethoxy-17β-(1-oxobutyl)-5-α-androst-3-ene for 20-α-(hydroxymethyl)-3-carbomethoxy-5-α-pregn-3-ene.

EXAMPLE 11

Androst-3,5-diene-17β-ol-3-carboxylic acid

The title compound is pepared according to Example 3 (iii through v) by substituting commercially available testosterone acetate for androst-4-ene-3-one-17β-N,N-diisopropylcarboxamide.

EXAMPLE 12

Androst-3,5-diene-17-one-3-carboxylic acid

The title compound is prepared according to Example 7 (i) by substituting androst-3,5-diene-17β-ol-3-carboxylic acid (Example 11) for 20-α-(hydroxymethyl)-3-carbomethoxy-5-α-pregn-3-ene.

EXAMPLE 13

Ethyl pregn-3,5,17(20)-triene-3-carboxy-21-oate

A solution of sodium ethoxide (680 mg, 10 mmol) in 5 ml ethanol is added to a mixture of androst-3,5-diene-17-one-3-carboxylic acid (942 mg, 3 mmol) prepared as in Example 12, and methyl diethylphosphonoacetate (2.12 g, 10 mmol) and the resulting mixture heated at reflux for 4 hours. The mixture is cooled, concentrated, diluted with dilute acetic acid and washed with ether. The combined ethereal extracts are washed with water and brine, and concentrated to yield ethyl pregn-3,5,17(20)-triene-3-carboxy-21-oate.

EXAMPLE 14

Androst-3,5,16-triene-17-N,N-dissopropylcarboxamide-3-carboxylic acid (i) Androst-3,5,16-triene-17-(trifluoromethylsulfonate)-3-carboxylic acid To a solution of androst-3,5-diene-17-one-3-carboxylic acid (314 mg, 1 mmol), prepared as in Example 12, in 10 ml methylene chloride is added 2,6-di-t-butyl-4-methylpyridine (272 mg, 1.5 mmol) and trifluoromethanesulfonic anhydride (0.3 ml, 1.6 mmol) and the solution is stirred for 4 hours. The reaction mixture is then diluted with methylene chloride, washed with 10% hydrochloric acid, brine, and concentrated to yield crude androst-3,5,16-triene-17-(trifluoromethylsulfonate)-3-carboxylic acid.

(ii) Androst-3,5,16-triene-17-N,N-diisopropylcarboxamide-3-carboxylic acid

A mixture of androst-3,5,16-triene-17-(trifluoromethylsulfonate)-3-carboxylic acid (447 mg, 1 mmol), triethylamine (200 mg, 2 mmol), diisopropylamine (4 g, 40 mmol), and bis(triphenylphosphine)palladium(II) acetate (22 mg, 0.03 mmol) in 4 ml DMF is stirred under an atmosphere of carbon monoxide for 4 hours. The mixture is then diluted with 10% hydrochloric acid and thoroughly washed with dichloromethane. The dichloromethane solution is washed with brine, dried and concentrated, and the residue is recrystallized (diethylether) to yield androst-3,5,16-triene-17-N,N-diisopropylcarboxamide-3-carboxylic acid.

EXAMPLE 15

2′,3′-α-Tetrahydrofuran-2′-spiro-17-(3,5-androstadiene-3-carboxylic acid

The title compound is prepared according to Example 3 (iii through v) by substituting 2′,3′-α-tetrahydrofuran-2′-spiro-17-(androst-4-ene-3-one) for androst-4-ene-3-one-17β-N,N-diisopropylcarboxamide.

EXAMPLE 16

3-Carbomethoxy-17β-acetamido-3,5-androstadiene

The title compound is prepared according to Example 3 (iii–iv) by substituting 17β-acetamido-4-androsten-3-one for androst-4-ene-3-one-17β-N,N-diisopropylcarboxamide.

EXAMPLE 17

Anrost-3,5-diene-17-α-ol-3,17β-dicarboxylic acid (i) 17β-Cyano-17-α-acetoxyandrost-4-ene-3-one 4-Androsten-3,17-dione (20 g) is dissolved by gentle warming in acetone cyanohydrin (30 ml). The crystals which form after several minutes are filtered, washed with pentane, and then dissolved in a mixture of pyridine (50 ml) and acetic anhydride (50 ml). After 48 hours the volatiles are removed under reduced pressure. The residue is then dissolved in ether and washed successively with 5% hydrochloric acid and aqueous sodium bicarbonate. The organic solution is dried and concentrated to afford a mixture of C-17 epimers of 17-cyano-17-acetoxyandrost-4-ene-3-one. Chromatography affords 17β-cyano-17-α-acetoxyandrost-4-ene-3-one.

(ii) 3-Carbomethoxy-17β-cyano-17-α-acetoxyandrost-3,5-diene

The title compound is prepared according to Example 3 (iii–iv) by substituting 17-cyano-17-acetoxyandrost-4-ene-3-one for androst-4-ene-3-one-17β-N,N-diisopropylcarboxamide.

(iii) Androst-3,5-diene-17-α-ol-3,17β-dicarboxylic acid

A solution of 3-carbomethoxy-17β-cyano-17α-acetoxyandrost-3,5-diene in methanol is cooled to 15° C. Dry hydrochloric acid is bubbled into the solution and the mixture allowed to stand at room temperature for 2 hours. Solvent is then removed under reduced pressure. A mixture of 1:1 THF-water is added followed by excess sodium hydroxide and the mixture is stirred for 2 hours. The reaction mixture then is acidified and extracted with chloroform. Concentration of the organic solution affords androst-3,5-diene-17-α-ol-3,17β-dicarboxylic acid which is recrystallized from methanol.

EXAMPLE 18

5-α-Androst-3,8(14)-diene-17β-ol-3-carboxylic acid (i) Androst-5,7-diene-3β,17β-diol A mixture of androst-5-ene-3β,17β-diol diacetate (3.75 g, 10 mmol), dibromantin (2.03 g, 7 mmol), and sodium bicarbonate (4.54 g, 54 mmol) in hexane (200 ml) is heated under reflux for 0.5 hours. The mixture is then cooled and filtered and the filtrate evaporated to dryness. The residue is dissolved in 50 ml toluene and treated with lithium bromide (2 g) in 5 ml of acetone. The mixture is stirred at 0° C. for 2 hours and then treated with 2 ml triethylamine and 1.5 ml benzenethiol. After stirring at room temperature for 1.5 hours, 100 ml ethyl acetate is added and the organic solution is washed with 1 N hydrochloric acid and water. The organic phase is dried and concentrated. The residue is then redissolved in 75 ml ethyl acetate, cooled to 0° C. and treated with 2.6 g of m-chloroperbenzoic acid for 2 hours. The mixture is washed with 10% sodium bicarbonate solution and then concentrated. The residue is dissolved in 100 ml toluene, treated with triethylamine (3.6 ml), heated at 70° C. for 24 hours, cooled, and washed with water. The organic solution was concentrated and chromatographed to yield androst-5,7-diene-3β,17β-diol diacetate. The diacetate is treated with $K_2CO_3$ in a 10:1 methanol:water solution overnight to yield, after extractive workup, androst-5,7-diene-3β,17β-diol.

(ii) Androst-4,7-diene-3,17-dione

A solution of androst-5,7-diene-3β,17β-diol (2.9 g, 10 mmol) in 150 ml toluene is azeotropically dried for one hour. Butanone (15 ml) is added followed by aluminum isopropoxide (1.7 g, 8 mmol) and the mixture is heated at reflux for 2.5 hours. The solution is then concentrated to a volume of 25 ml, diluted with trichloromethane, and washed with 5% hydrochloric acid, aqueous sodium bicarbonate, and brine. Concentration and chromatography affords androst-4,7-diene-3,17-dione.

(iii) 5-α-Androst-7-ene-3-one-17β-ol

The title compound is prepared according to the procedure of Example 4 (i) by substituting androst-4,7-diene-3,17-dione for 3-oxo-17β-(hydroxymethyl)-4-androstene.

(iv) 5-α-Androst-8(14)-ene-3-one-17β-ol

A solution of 5-α-androst-7-ene-3-one-17β-ol in ethyl acetate is hydrogenated at room temperature and 1 atmosphere over 10% palladium on carbon for 8 hours. Filtration to remove the catalyst and concentration affords 5-α-androst-8(14)-ene-3-one-17β-ol.

(v) 5-α-androst-1,8(14)-diene-3-one-17β-ol

The title compound is prepared according to Example 5 (ii) by substituting 5-α-androst-8(14)-ene-3-one-17β-ol for 20-α-(hydroxymethyl)-5-α-pregnan-3-one.

(vi) 5-α-Androst-3,8(14)-diene-17β-ol-3-carboxylic acid

The title compound is prepared according to Example 5 (v through x) by substituting 5-α-androst-1,8(14)-diene-3-one-17β-ol for 20-α-(hydroxymethyl)-pregn-4-ene-3-one.

EXAMPLE 19

N,N-Diisopropyl androst-3,5,7-triene-17β-carboxamide-3-carboxylic acid (i) Androst-4,6-diene-3-one-17β-N,N-diisopropylcarboxamide Androst-4-ene-3-one-17β-N,N-diisopropylcarboxamide (12 , 30 mmol) and chloranil (8.95 g, 36.4 mmol) in 700 ml t-butanol is heated at reflux for 3.5 hours then cooled and filtered. The filtrate is concentrated and the residue taken up in 700 ml trichloromethane and washed successively with 4×150 ml water, 3×150 ml aqueous sodium bicarbonate, 3×150 ml 5% sodium hydroxide, 3×150 ml brine, dried over sodium sulfate and concentrated to yield androst-4,6-diene-3-one-17β-N,N-diisopropylcarboxamide.

(ii) N,N-Diisopropyl androst-3,5,7-triene-17β-carboxamide-3carboxylic acid

The title compound is prepared according to Example 3 (iii-v) by substituting androst-4,6-diene-3-one-17β-N,N-diisopropylcarboxamide for androst-4-ene-3-one-17β-N,N-diisopropylcarboxamide.

EXAMPLE 20

N,N-Diisopropyl-4-chloro-androst-3,5-diene-17β-carboxamide-3-carboxylic acid (i) 3-Oxo-androstane-4-5-α-epoxide-17β-N,N-diisopropylcarboxamide The title compound is prepared according to Example 4 (v) by substituting androst-4-ene-3-one-17β-N,N-diisopropylcarboxamide for 3-oxo-5-α-androst-1-ene-17β-N,N-diisopropylcarboxamide.

(ii) 3-Oxo-4-chloro-4-androstene-17β-N,N-diisopropylcarboxamide

A stream of hydrogen chloride gas is passed through a chloroform solution of 3-oxo-androstane-4,5-α-epoxide-17β-N,N-diisopropylcarboxamide for 2 minutes. The solution is then washed with water, dried ($Na_2SO_4$), and concentrated to yield 3-oxo-4-chloro-4-androstene-17β-N,N-diisopropylcarboxamide.

(iii) N,N-diisopropyl-4-chloro-androst-3,5-diene-17β-carboxamide-3-carboxylic acid The title compound is prepared according to Example 3 (iii through v) by substituting 3-oxo-4-chloro-4-androstene-17β- N,N-diisopropylcarboxamide for androst-4ene-3one-17β-N,N-diisopropylcarboxamide.

EXAMPLE 21

N,N-Diisopropyl-4-methyl-5-α-androst-3-ene-17β-carboxamide-3carboxylic acid (i) 3-Oxo-17β-(hydroxymethyl)-4-methyl-4-androstene A mixture of potassium-t-butoxide (5 g) in 100 ml t-butanol is heated to reflux. A solution of 3-oxo-17β-(hydroxymethyl)-4-androstene (10 g) in t-butanol is added followed by a solution of methyl iodide (2.7 g) in t-butanol. Heating is continued for 3 hours. The mixture is then cooled, acidified, and extracted with dichloromethane. The dichloromethane solution is washed with brine, dried, and concentrated to yield 3-oxo-17β-(hydroxymethyl)-4-methyl-4-androstene.

(ii) N,N-Diisopropyl-4-methyl-5-α-androst-3-ene-17β-carboxamide-3-carboxylic acid The title compound is prepared according to Example 2 (iii through viii) by substituting 3-oxo-17β-(hydroxymethyl)-4-methyl-4-androstene for 3-oxo-17β-(hydroxymethyl)-4-androstene.

EXAMPLE 22

N,N-Diisopropyl-4-trifluoromethyl-androst-3,5-diene-17β-carboxamide-3-carboxylic acid (i) 3-Oxo-4-trifluoromethyl-4-androstene-17β-N,N-diisopropylcarboxamide A solution of 3-oxo-4-androstene-17β-N,N-diisopropylcarboxamide (1 g) in 10 ml of pyridine is cooled to −78° C. Trifluoromethyl iodide gas is condensed in a dry ice-acetone bath and added to the steroid-pyridine cooled solution. The resulting solution is photolyzed using a medium pressure 450 watt mercury vapor lamp at room temperature for 18 hours. The reaction mixture is then diluted with ethyl acetate, washed with cold dilute hydrochloric acid, 5% sodium bisulfite, water, brine, dried over, anhydrous sodium sulfate, and concentrated to dryness. Purification on a silica gel column eluting with 20% ethyl acetate in hexane yields 3-oxo-4-trifluoromethyl-4-androstene-17β-N,N-diisopropylcarboxamide.

(ii) N,N-Diisopropyl4-trifluoromethyl-androst-3,5-diene-17β-carboxamide-3carboxylic acid The title compound is prepared according to Example 3 (iii through v) by substituting 3-oxo-4-trifluoromethyl-4-androstene-17β-N,N-diisopropylcarboxamide for androst-4-ene-3-one-17β-N,N-diisopropylcarboxamide.

EXAMPLE 23

N,N-Diisopropyl-6-trifluoromethyl-androst-3,5-diene-17β-carboxamide-3-carboxylic acid (i) 3-Oxo-6-trifluoromethyl-43-androstene-17β-N,N-diisopropylcarboxamide 17β-N,N-diisopropylcarboxamide-3-(trifluoromethylsulfonate)-androst-3,5-diene (1 g) is dissolved in 10 ml of pyridine and is photolyzed using a Hanovia medium pressure 450 watt mercury vapor lamp at room temperature for 18 hours. The reaction solution is diluted with ethyl acetate which in turn is washed with cold dilute hydrochloric acid, water, brine, dried over anhydrous magnesium sulfate, and evaporated to dryness. Silica gel column chromatography eluting with 20% ethyl acetate in hexane affords 3-oxo-6-trifluoromethyl-4-androstene-17β-N,N-diisopropylcarboxamide.

(ii) N,N-Diisopropyl-6-trifluoromethyl-androst-3,5-diene-17β-carboxamide-3-carboxylic acid The title compound is prepared according to Example 3 (iii through v) by substituting 3-oxo-6-trifluoromethyl-4-androstene-17β-N,N-diisopropylcarboxamide for androst-4-ene-3-one-17β-N,N-diisopropylcarboxamide.

EXAMPLE 24

17β-N,N-Diisopropylcarboxamide-6-fluoro-androst-3,5-diene-3-carboxylic acid (i) 17β-N,N-Diisopropylcarboxamide-5-α-androstene-3-spiro-2′-dioxolane To a solution of 3-oxo-4-androstene-17β-N,N-diisopropylcarboxamide (8 g) in 300 ml of benzene was added 30 ml of ethylene glycol and p-toluenesulfonic acid (240 mg). The resulting solution was refluxed under argon with water collection using a Dean Stark trap for 30 hours. The reaction mixture was then allowed to cool to room temperature and diluted with ethyl acetate. The organic layer was washed with 5% sodium bicarbonate, brine, dried over anhydrous magnesium sulfate, and evaporated to dryness. The crude material was purified on a silica gel column using 20% ethyl acetate in hexane as the eluting solvent to afford 7 g of 17β-N,N-diisopropylcarboxamide-5-α-androstene-3-spiro-2′-dioxolane (80%).

(ii) 17β-N,N-Diisopropylcarboxamide-5-α-6-α-epoxyandrostane-3-spiro-2′-dioxolane To a solution of 17β-N,N-diisopropylcarboxamide-5-androstene-3-spiro-2'-dioxolane (4.43 g, 10 mmol) in 100 ml of dry dichloromethane at 0° C. was added a solution of m-chloroperbenzoic acid (2.8 g) in 40 ml of dichloromethane dropwise through a dropping funnel. After completion of addition of m-chloroperbenzoic acid, the reaction mixture was allowed to warm to room temperature and stirred for another 30 minutes. The reaction mixture and then washed with 10% aqueous sodium sulfite solution four times followed by 5% aqueous sodium bicarbonate solution, brine, dried over anhydrous magnesium sulfate, and concentrated to a syrup. Column chromatography, eluting with 30% ethyl acetate in hexane, yielded 2.76 g of 17β-N,N-diisopropylcarboxamide-5-α, 6-α-epoxyandrostane-3-spiro-2'-dioxolane as a white solid (61%).

(iii) 3-Oxo-6-fluoro-4-androstene-17β-N,N-diisopropylcarboxamide

17β-N,N-diisopropylcarboxamide-5-α, 6-α-epoxyandrostane-3-spiro-2'-dioxolane (2.5 g) was dissolved in a mixture of 50:50 (v/v) benzene and ether. To this solution was added borontrifluoride-etherate (2.5 ml) under argon. The reaction solution was stirred at room temperature under argon for four hours and then quenched with 5% aqueous sodium carbonate. The organic layer was washed with water, brine, dried over anhydrous magnesium sulfate, and evaporated to dryness over reduced pressure. The residue was then treated with 15 ml of saturated hydrogen chloride in glacial acetic acid. The resulting solution was stirred at room temperature under argon for 1.5 hours and then diluted with ethyl acetate. The ethyl acetate solution was washed with 5% aqueous sodium bicarbonate, water, brine, dried over anhydrous magnesium sulfate, and evaporated to dryness. The crude material was purified on a silica gel column eluting with 25% ethyl acetate in hexane to yield 3-oxo-6β-fluoro-4-androstene-17β-N,N-diisopropylcarboxamide (675 mg, 30%) and 3-oxo-6-α-fluoro-4-androstene-17β-N,N-diisopropylcarboxamide (900 mg, 40%).

(iv) 17β-N,N-Diisopropylcarboxamide-3-(trifluoromethylsulfonate)-6-fluoro-androst-3,5-diene To a solution of the epimers of 3-oxo-6-fluoro-4-androstene-17β-N,N-diisopropylcarboxamide (1.4 g) in 50 ml of dry dichloromethane was added 2,6-di-t-butyl-4-methylpyridine (850 mg) followed by trifluoromethanesulfonic anhydride (0.75 ml) under argon. The resulting solution was stirred at room temperature under argon for 3 hours. The solvent was then removed under reduced pressure. The residue was redissolved in ethyl acetate which in turn was washed with cold dilute hydrochloric acid, water, brine, dried over anhydrous magnesium sulfate, and evaporated to an oil. Column chromatography (silica gel, 10% ethyl acetate in hexane) yielded 17β-N,N-diisopropylcarboxamide-3-(trifluoromethylsulfonate)-6-fluoro-androst-3,5-diene and 17β-N,N-diisopropylcarboxamide-3-(trifluoromethylsulfonate)-6-fluoro-androst-2,4-diene.

(v) Ethyl 17β-N,N-diisopropylcarboxamide-6-fluoroandrost-3,5-diene-3-carboxylate A mixture of 17β-N,N-diisopropylcarboxamide-3-(trifluoromethylsulfonate)-6-fluoro-androst-3,5-diene (250 mg), triethylamine (0.12 ml), ethanol (1.5 ml), N,N-dimethylformamide (2 ml) and bis(triphenylphosphine)-palladium(II) acetate (25 mg) was purged with carbon monoxide for 10 minutes. The reaction mixture was stirred under one atmosphere of carbon monoxide at room temperature overnight and then diluted with ethyl acetate. The ethyl acetate solution was then washed with cold dilute hydrochloric acid, water, brine, dried over anhydrous magnesium sulfate, and concentrated to dryness. Silica gel column chromatography eluting with 10% ethyl acetate in hexane yielded 108 mg of ethyl 17β-N,N-diisopropylcarboxamide-6-fluoro-androst-3,5-diene-3-carboxylate (55%).

(vi) 17β-N,N-Diisopropylcarboxamide-6-fluoroandrost-3,5-diene-3-carboxylic Acid

The title compound was prepared according to Example 2 (viii) by substituting ethyl 17β-N,N-diisopropylcarboxamide-6-fluoro-androst-3,5-diene-3-carboxylate for 3-carbomethoxy-3-androstene-17β-N,N-diisopropylcarboxamide. The product had a melting point of 225°-226° C. (recrystallized from acetonitrile).

EXAMPLE 25

N-t-Butyl Androst-3,5-diene-17β-carboxamide-3-Carboxylic Acid (i) Androst-4-ene-3-one-17β-N-t-Butyl Carboxamide The title compound was prepared according to Example 3(ii) by using tert-butylamine in place of diisopropylamine.

(ii) 17β-(N-t-butylcarboxamide)-3-(trifluoromethyl sulfonate)-androst-3,5-diene

The title compound was prepared in 45% yield according to Example 3(iii) by using androst-4-ene-3-one-17β-t-butylcarboxamide in place of androst-4-ene-3-one-17β-N,N-diisopropyl carboxamide.

(iii) 3-Carbomethoxyandrost-3,5-diene-17β-N-t-butylcarboxamide

The title compound was prepared according to Example 3(iv) by using 17β-(N-t-butylcarboxamide)-3-(trifluoromethylsulfonate)-androst-3,5-diene in place of 17β-(N,N-diisopropylcarboxamide)-3-(trifluoromethylsulfonate)-androst-3,5-diene.

(iv) N-t-Butyl Androst-3,5-diene-17β-carboxamide-3-carboxylic Acid

The title compound was prepared according to Example 3(v) by using 3-carbomethoxyandrost-3,5-diene-17β-N-t-butylcarboxamide in place of 3-carbomethoxyandrost-3,5-diene-17β-N,N-diisopropylcarboxamide. The title compound was recrystallized from acetonitrile, m.p. 247°-250°.

EXAMPLE 25A

N-t-Butyl Androst-3,5-diene-17β-carboxamide-3-Carboxylic Acid (i) N-t-Butyl Androst-3,5-diene-3-bromo-17β-carboxamide To an ice cooled solution of 3-oxo-androst-4-ene-17-carboxylic acid (10 g, 30 mmol) in toluene (100 mL) was added a solution of oxalyl bromide (24.2 g, 11 mL, 112 mmol) in toluene (100 mL). The reaction miture was warmed to room temperature until gas evolution ceased.

Excess oxalyl bromide was evaporated at room temperature and the residual androst-3,5-diene-3-bromo-17β-acid bromide in toluene solution was ice cooled. T-butyl amine (40 mL) in toluene (70 mL) was slowly added and the mixture was stirred 19 hours.

The reaction mixture was diluted with water (200 mL) and toluene (100 mL). The organic soluble material was separated and washed with water (2×250 mL), dried over magnesium sulfate, and evaporated. The oil/solid reside was flash chromatographed using silica gel, flash grad, eluting with 5:1 hexane ethyl acetae to give 5.5 g of white solid, mp 174°–77° C. (40.3%).

(ii) N-t-Butyl Androst-3,5-diene 17β-carboxamide-3-carboxylic Acid

N-Butyl lithium (2.5M in hexane, 90 mL, 225 mmol) was added over 20 minutes to a solution of androst-3,5-diene-3-bromo-17β-N-t-butylcarboxamide (25 g, 57.7 mmol) in dry tetrahydrofuran (650 mL) cooled in −64° C. After 2.5 hours the reaction mixture was quenched with dry $CO_2$ for one hour, diluted with toluene (500 mL), 10% hydrochloric acid solution (100 mL), and water (500 mL). The organic soluble extract was separated, washed with water (2×300 mL), dried over magnesium sulfate and evaporated. The crude off-white solid was recrystallized from ethyl acetate to give 3.5 g of white solid, mp 242°–249° C.

EXAMPLE 25B

N-t-Butyl Androst-3,5-diene-17β-carboxamide-3-carboxylic acid (i) Methyl Androst-3,5-diene-3-bromo-17β-carboxylate Methyl androst-4-ene-17β-carboxylate (100 g, 316 mmol) wa dissolved in glacial acetic acid (500 mL), and phosphorous tribromide (119 g, 80 ml, 440 mmol) was added over 15 minutes. After stirring at room temperature for 2 hours, the yellow precipitate that formed was filtered, washed with methanol (400 mL), and dried in vacuo to give 97.6 g (81.4%) of white solid, mp 178°–180° C.

(ii) Androst-3,5-diene-3-bromo-17β-carboxylic Acid

A solution of potassium hydroxide (50 g, 890 mmol) in 9:1 methanol: water (500 mL) was added to a slurry of methyl androst-3,5-diene-3-bromo-17β-carboxylate. After refluxing 41 hours, the resultant yellow solution was cooled and brought to pH 4 using 10% hydrochloric acid solution. The white solid that formed was filtered and washed with water. After drying in vacuo at 40° C., 49 g (100%) of product, mp 248°–250° C. was obtained.

(iii) N-t-Butyl Androst-3,5-diene-3-bromo-17β-carboxamide

Oxalyl chloride (17 mL, 190 mmol) was added to a cooled mixture of androst-3,5-diene-3-bromo-17β-carboxlic acid (30 g, 79 mmol) in dry toluene (300 mL) over 14 minutes. The reaction mixture was stirred at room temperature until gas evolution ceased (about 1.5 hours).

Excess oxalyl chloride was removed by concentration in vacuo at room temperature. The reaction mixture was ice cooled and t-butylamine (102 mL, 954 mmol) was added over 10 minutes. The reactant mixture was stirred at room temperature for 1.5 hours.

The mixture was diluted with water (300 mL) and toluene (50 mL). The organic layer was separated, washed with water (2×300 mL), dried over magnesium sulfate and evaporated. The resultant pale yellow solid was slurried first methanol:water (7.3, 200 mL) then acetonitrile:water (39:11, 300 mL). After filtration and drying in vacuo, 33.2 (77.5%) of white solid product was obtained.

(iv) N-t-Butyl Androst-3,5-diene-17β-carboxamide-3-carboxylic Acid

N-Butyl lithium (2.5M in hexane, 90 mL, 225 mmol) was added over 20 minutes to a solution of N-t-butylandrost-3,5-diene-3-bromo-17β-carboxamide (25 g. 57.7 mmol) in dry tetrahydrofuran (650 mL) cooled to −1° C. After 2.5 hours the reaction mixture was quenched with dry $CO_2$ for one hour, diluted with toluene (500 mL), 10% hydrochloric acid solution (100 mL), and water (500 mL). the organic soluble extract was separated, washed with water (2×200 mL), dried over magnesium sulfate and evaporated. The crude off-white solid was recrystallized from ethyl acetate to give 3.5 g of white solid, mp 242°–249° C.

EXAMPLE 25C

N,N-Diisopropyl-androst-3,5-diene-17β-carboxamide-3-carboxylic Acid

The title compound was prepared by substituting diisopropylamine for t-butylamine in the process of Example 25B.

EXAMPLE 25D

Androst-3,5-diene-3-methoxycarbonyl-17β-t-butylcarboxamide

A mixture of N-t-butyl-androst-3,5-diene-3-bromo-17β-carboxamide (42 mg), prepared as in Example 25B, palladium (II) acetate (20 mg), triphenylphosphine (40 mg), methanol (5 mL), dimethyl formamide (5 mL), and triethylamine (3 mL) was heated at 85°–95° C. under a carbon monoxide atmosphere until the starting material disappeared. The title compound was isolated by flash chromatography on silica gel with 6:1 hexane:ethyl acetate.

EXAMPLE 25E

Androst-3,5-diene-3-Methoxycarbonyl-17β-N,N-diisopropylcarboxamide

The title compound is prepared according to Example 25D, substituting N,N-diisopropylamine for N-t-butylamine.

EXAMPLE 26

N,N-Diisopropyl 5-α-Androst-2-ene-17β-carboxamide-3-carboxylic Acid (i) 17β-(N,N-Diisopropylcarboxamide)-3-(trifluoromethylsulfonate)-5α-androst-2-ene The title compound was prepared according to Example 4(vii) by using 3-oxo-5α-androstane-17β-N,N-diisopropylcarboxamide in place of 3-oxo-4-fluoro-5α-androst-1-ene-7β-N,N-diisopropyl.

(ii) 3-Carbomethoxy-5α-Androst-2-ene-17β-N,N-diisopropylcarboxamide

The title compound was prepared according to Example 3(iv) by using 17β-(N,N-diisopropylcarboxamide)-3-(trifluoromethylsulfonate)-5α-androst-2-ene in place of 17β-(N,N-diisopropylcarboxamide)-3-(trifluoromethylsulfonate)androst-3,5-diene.

(iii) N,N-Diisopropyl 5α-Androst-2-ene-17β-carboxamide-3-carboxylic Acid

The title compound was prepared according to Example 3(v) by using 3-carbomethoxy-5α-androst-2-ene-17β-N,N-diisopropylcarboxamide in place of 3-carbomethoxyandrost-3,5-diene-17β-N,N-diisopropylcarboxamide. The title compound was recrystallized from acetonitrile; m.p. 203°–205°.

EXAMPLE 27

N,N-Diisopropyl Androst-2,4-diene-17β-carboxamide-3-carboxylic Acid (i) 17β-(N,N-Diisopropylcarboxamide)-3-trifluoromethylsulfonate)androst-2,4-diene The title compound was prepared according to Example 4(vii) by using 3-oxoandrost-4-ene-17β-N,N-diisopropylcarboxamide in place of 3-oxo-4-fluoro-5-α-androst-1-ene-17β-N,N-diisopropylcarboxamide. The title compound was recrystallized from methanol; m.p. 165°-168°.

(ii) 3-Carbomethoxyandrost-2,4-diene-17β-N,N-diisopropylcarboxamide

The title compound was prepared according to Example 3(iv) by using 17β-(N,N-diisopropylcarboxamide)-3-(trifluoromethylsulfonate)androst-2,4-diene in place of 17β-(N,N-diisopropylcarboxamide)-3-(trifluoromethylsulfonate)-androst-3,5-diene. The title compound had a melting point of 162° after trituration with methanol.

(iii) N,N-Diisopropyl Androst-2,4-diene-17β-carboxamide-3-carboxylic Acid

The title compound was prepared according to Example 3(v) by using 3-carbomethoxy-androst-2,4-diene-17β-N,N-diisopropylcarboxamide in place of 3-carbomethoxy-androst-3,5-diene-17β-N,N-diisopropylcarboxamide. The title compound was recrystallized from methanol-acetone; m.p. 227°.

EXAMPLE 28

N,N-Diisopropyl 5α-Androstane-17β-carboxamide-3β-carboxylic Acid (i) 3β-Carbomethoxy-5α-androstane-17β-N,N-diisopropylcarboxamide 3-Carbomethoxy-5-α-androst-2-ene-17β-N,N-diisopropylcarboxamide (87 mg, 0.19 mmol) (Example 26, (ii) in 15 ml of a 10:1 solution of ethyl acetate and acetic acid was hydrogenated at 25° and 1 atm over 20 mg 10% Pd on carbon. The solution was filtered to remove the catalyst and concentrated to yield 77 mg (88%) of the title compound.

(ii) N,N-Diisopropyl 5-α-Androstane-17β-carboxamide-3β-carboxylic Acid

The title compound was prepared according to Example 3(v) by using 3β-carbomethoxy-5α-androstane-17β-N,N-diisopropylcarboxamide in place of 3-carbomethoxyandrost-3,5-diene-17β-N,N-diisopropylcarobxamide. The title compound was recrystallized from acetonitrile; m.p. 142°-144° C.

EXAMPLE 29

N,N-Diisopropyl Estr-3,5(10)-diene-17β-carboxamide-3-carboxylic Acid (i) 3-Methox-estr-1,3,5(10),16-tetraene-17-N,N-diisopropylcarboxamide The title compound was prepared according to the two steps of Example 3(iii, iv) by using methyl estrone in place of androst-4-ene-3-one-17β-N,N-diisopropylcarboxamide and diisopropylamine in place of methanol.

(ii) 3-Methoxy-estr-1,3,5(10)-triene-17β-N,N-diisopropylcarboxamide

3-Methox-estr-1,3,5(10),16-tetraene-17-N,N-diisopropylcarboxamide (4.45 g, 11.3 mmol) in 100 ml of a 3:1 solution of ethyl acetate and ethanol was hydrogenated at 25° and 1 atm. over PtO₂ (350 mg) for 6 hours. The solution was filtered to remove the catalyst and concentrated to afford 4.36 g (98%) of the title compound.

(iii) 3-Oxo-estr-5(10)-ene-17β-N,N-diisopropylcarboxamide

To a solution of 3-methoxyestr-1,3,5(10)-triene-17β-N,N-diisopropylcarboxamide (1.4 g, 3.5 mmol) in liquid ammonia (25 ml), THF (10 ml), and t-butanol (10 ml) at −33° C. was added 0.5 g of lithium wire. The solution was stirred for 5 hours and then methanol (10 ml) was slowly added. The ammonia was allowed to evaporate and the residue was then partitioned between water and chloroform. The organic phase was concentrated to a white solid which was suspended in a methanol-water mixture and then treated with 1.4 g oxalic acid for 1.5 hours. The reaction mixture was then diluted with water and extracted with ethyl acetate. The organic phase was concentrated and the residue chromatographed (silica, 1:9 ethyl acetate-hexane) to yield 0.4 g of the title compound.

(iv) N,N-Diisopropyl Estr-3,5(10)-diene-17β-carboxamide-3-carboxylic Acid

The title compound was prepared according to Example 26, (i-iii), by using 3-oxoestr-5(10)-ene-17β-N,N-diisopropylcarboxamide for 3-oxo-5-α-androstane-17β-N,N-diisopropylcarboxamide. The title compound was recrystallized from acetonitrile; m.p. 250°-253° C.

EXAMPLE 30

N,N-Diisopropyl Estr-3,5-diene-17β-carboxamide-3-carboxylic Acid (i) 3-Oxoestr-4-ene-17β-N,N-diisopropylcarboxamide 3-Oxoestr-5(10)-ene-17β-N,N-diisopropylcarboxamide (Example 26, (iii) was dissolved in methanol and 10% aqueous HCl (2:1) and heated at 65° for 1 hour, cooled, and thoroughly extracted with chloroform. The organic extracts were concentrated to yield the title compound as a white solid.

(ii) N,N-Diisopropyl Estr-3,5-diene-17β-carboxamide-3-carboxylic Acid

The title compound was prepared according to Example 3(iii-v) by using 3-oxo-estr-4-ene-17β-N,N-diisopropylcarboxamine in place of androst-4-ene-3-one-17β-N,N-diisopropylcarboxamide. The title compound had a melting point of 215° C.

EXAMPLE 31

17β-(N,N-Diisopropylcarboxamide)-Androst-3,5,11-triene-17β-carboxylic Acid (i) Androst-4-ene-3-one-11-ol-17β-carboxylic Acid Corticosterone is dissolved in methanol and treated with an aqueous solution of periodic acid at room temperature for 18 hours. The solution is then diluted with water to induce precipitation of androst-4-ene-3-one-11-ol-17β-carboxylic acid which is collected by filtration.

(ii) Androst-4-ene-3,11-dione-17β-carboxylic Acid

To a solution of androst-4-ene-3-one-11-ol-17β-carboxylic acid in acetone is added Jones Reagent dropwise until a red color persists. Isopropanol is then added to quench the excess oxidant. The solution is decanted and the residual chromium salts are thoroughly washed with acetone. The combined organic solutions are then filtered through magnesium sulfate and concentrated to yield androst-4-ene-3,11-dione-17β-carboxylic acid.

(iii) Androst-4-ene-3,11-dione-17β-(N,N-diisopropylcarboxamide)

The title compound is prepared according to Example 3 (ii) by substituting androst-4-ene-3,11-dione-17β-carboxylic acid for androst-4-ene-3-one-17β-carboxylic acid.

(iv) 17β-(N,N-Diisopropylcarboxamide)-3-(trifluoromethylsulfonate)-11-oxo-androst-3,5-diene The title compound is prepared according to Example 3 (iii) by substituting androst-4-ene-3,11-dione-17β-(N,N-diisopropylcarboxamide) for an androst-4-ene-3-one-17β-(N,N-diisopropylcarboxyamide).

(v) 3-Carbomethoxy-11-oxo-androst-3,5-diene-17β-(N,N-diisopropylcarboxamide)

The title compound is prepared according to Example 3 (iv) by substituting 17β-(N,N-diisopropylcarboxamide)-3-(trifluoromethylsulfonate)-11-oxo-androst-3,5-diene for 17β-(N,N-diisopropylcarboxamide)-3-(trifluoromethylsulfonate)-androst-3,5-diene.

(vi) 3-Carbomethoxy-11-(trifluoromethylsulfonate)-androst-3,5,11-triene-17β-(N,N-diisopropylcarboxamide)

The titled compound is prepared according to Example 4(vi) by substituting 3-carbomethoxy-11-oxo-androst-3,5-diene-17β-(N,N-diisopropylcarboxamide) for 3-oxo-4-fluoro-5-α-androst-1-ene-17β-(N,N-diisopropyl-carboxamide).

(vii) 3-Carbomethoxy-androst-3,5,11-triene-17β-(N,N-diisopropylcarboxamide)

The title compound is prepared according to the procedure of Cacchi (Tet. Lett. 25 (42) 4821–4824 (1984)) by substituting 3-carbomethoxy-11-(trifluoromethylsulfonate)-androst-3,5,11-triene-17β-(N,N-diisopropylcarboxamide) for 17β-acetoxyandrost-3,5-diene-3-yl triflate.

(viii) 17β-(N,N-Diisopropylcarboxamide)-androst-3,5,11-triene-3-carboxylic acid

The title compound is prepared according to Example 3(v) by substituting 3-carbomethoxy-androst-3,5,11-triene-17β-(N,N-diisopropylcarboxamide) for 3-carbomethoxy-androst-3,5-diene-17β-(N,N-diisopropylcarboxamide).

EXAMPLE 32

17β-(N-t-Butylcarboxamide)-androst-3,5,11-triene-3-carboxylic acid

The process of Example 31 wherein N-t-butylamine is used in place of diisopropylamine yields 17β-(N-t-Butylcarboxamide)-androst-3,5,11-triene-3-carboxylic Acid.

EXAMPLE 33

17β-(N,N-diisopropylcarboxamide)-androst-3,5-diene-3-thiocarboxylic Acid

A solution of 17β-(N,N-diisopropylcarboxamide)-androst-3,5-diene-3-carboxylic acid (1 mmol) is suspended in 10 mL toluene and treated with 0.5 mL of oxalyl chloride for two hours. The resulting solution is then slowly added to a solution of THF and hydrogen sulfide through which hydrogen sulfide is bubbled. The mixture is then diluted with ethyl acetate, washed with water, dried and concentrated, the residue is recrystallized from acetonitrile to yield the title compound.

EXAMPLE 34

17β-(N-t-Butylcarboxamide)-androst-3,5-diene-3-thiocarboxylic Acid

The process of Example 33 wherein 17β-(N,N-diisopropylcarboxamide)-androst-3,5-diene-3-carboxylic acid is replaced by 17β-(N-t-Butylcarboxamide)-androst-3,5-diene-3-thiocarboxylic Acid.

EXAMPLE 35-44

The following compounds are prepared by substituting diisopropylamine for t-butylamine using the procedures of examples 2, 3, 4, 6, 24, 26, 27, 28, 29 and 30, respectively:

N-t-Butyl-5-α-androst-3-ene-17β-carboxamide-3-carboxylic acid;

17β-(N-t-Butylcarboxamide)-6-fluoro-5-α-androst-3-ene-3-carboxylic acid;

17β-(N-t-Butylcarboxamide)-6-fluoro-androst-3,5-diene-3-carboxylic acid;

3-Carbomethoxy-N-t-butyl-androst-3,5-diene-17β-carboxamide,

17β-N-t-Butylcarboxamide-5-α-androst-1,3-diene-3-carboxylic acid;

N-t-Butyl-5-α-androst-2-ene-17β-carboxamide-3-carboxylic acid;

N-t-Butyl-androst-2,4-diene-17β-carboxamide-3-carboxylic acid;

N-t-Butyl-5-α-androstane-17β-carboxamide-3-carboxylic acid;

N-t-Butyl-estr-3,5,(10)-diene-17β-carboxamide-3-carboxylic acid; and

N-t-Butyl-estr-3,5-diene-17β-carboxamide-3-carboxylic acid.

EXAMPLE 45

An oral dosage form for administering Formula (III) compounds is produced by screening, mixing, and filling into hard gelatin capsules the ingredients in the proportions shown in Table V, below.

TABLE V

| Ingredients | Amounts |
| --- | --- |
| 20-α-(Hydroxymethyl)-5-α-pregn-3-ene-3-carboxylic acid | 50 mg |
| magnesium stearate | 5 mg |
| lactose | 75 mg |

EXAMPLE 46

The sucrose, calcium sulfate dihydrate and Formula (III) compound shown in Table VI below, are mixed and granulated in the proportions shown with a 10% gelatin solution. The wet granules are screened, dried, mixed with the starch, talc and stearic acid, screened and compressed into a tablet.

TABLE VI

| Ingredients | Amounts |
| --- | --- |
| N,N-Diisopropyl-5-α-androst-3-ene-17β-carboxamide-3-carboxylic acid | 100 mg |
| calcium sulfate dihydrate | 150 mg |
| sucrose | 20 mg |
| starch | 10 mg |
| talc | 5 mg |
| stearic acid | 3 mg |

EXAMPLE 47

20-α-(Hydroxymethyl)-4-fluoro-5-α-pregn-3-ene-3-carboxylic acid, 75 mg, is dispursed in 25 ml of normal saline to prepare an injectable preparation.

While the preferred embodiments of the invention are illustrated by the above, it is to be understood that the invention is not limited to the precise instructions herein disclosed and that the right to all modifications coming within the scope of the following claims is reserved.

What is claimed is:

1. A compound represented by the formula:

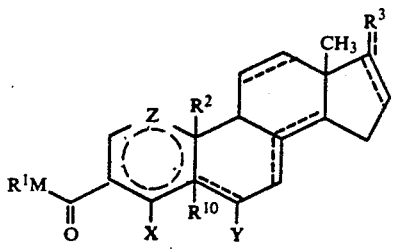 (I)

in which:

The A ring has up to 2 double bonds;

The B, C and D rings have optional double bonds where indicated by the broken lines, provided that the A-B rings and the B-C rings do not have adjacent double bonds and the D ring does not have a $C_{16}$–$C_{17}$ double bond when $R^3$ represents two substituents or a divalent substituent;

M is O or S;

Z is $CH_2$ or, when part of a double bond, CH;

X is H, Cl, F, Br, I, $CF_3$, or $C_{1-6}$alkyl;

Y is H, $CF_3$, F, or Cl, $CH_3$, provided that Y is H when there is no $C_5$–$C_6$ double bond;

$R^1$ is H or $C_{1-8}$alkyl;

$R^2$ is absent or present as H or $CH_3$ provided $R^2$ is absent when the carbon to which it is attached is double bonded;

$R^{10}$ is absent when there is a $C_4$–$C_5$, $C_5$–$C_6$, or $C_5$–$C_{10}$ double bond, or present as an alpha hydrogen; and $R^3$ is (1) α-hydrogen, α-hydroxyl, or α-acetoxy and/or (a)

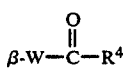

where W is a bond or $C_{1-12}$alkyl, and $R^4$ is (i) hydrogen,
(ii) hydroxyl,
(iii) $C_{1-8}$alkyl,
(iv) hydroxy $C_{1-8}$alkyl,
(v) $C_{1-8}$alkoxy,
(vi) $NR^5R^6$, where $R^5$ and $R^6$ are each independently selected from hydrogen, $C_{1-8}$alkyl, $C_{3-6}$cycloalkyl, phenyl; or $R^5$ and $R^6$ taken together with the nitrogen to which they are attached represent a 5–6 membered saturated ring comprising up to one other heteroatom selected from oxygen and nitrogen, or
(vii) $OR^7$, where $R^7$ is hydrogen, alkali metal, $C_{1-18}$alkyl, benzyl, or (b) β-Alk-$OR^8$, where Alk is $C_{1-12}$alkyl, and $R^8$ is (i) phenyl$C_{1-6}$alkylcarbonyl,
(ii) $C_{5-10}$cycloalkylcarbonyl,
(iii) benzoyl,
(iv) $C_{1-8}$alkoxycarbonyl,
(v) aminocarbonyl, or $C_{1-8}$alkyl substituted aminocarbonyl,
(vi) hydrogen, or
(vii) $C_{1-8}$alkyl, (2) =CH—W—CO—$R^4$ or =CH—W—$OR^8$, where W is a bond or $C_{1-12}$alkyl and $R^4$ and $R^8$ have the same meaning as above and $R^8$ also is hydrogen or $C_{1-20}$alkylcarbonyl;

(3)

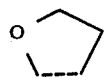

where the dashed bond replaces the 17-α-hydrogen, (4) α-hydrogen and β-NHCOR$^9$ where $R^9$ is $C_{1-12}$alkyl or β-$NR^5R^6$ where $R^5$ and $R^6$ have the same meaning as above, (5) α-hydrogen and β-cyano, (6) α-hydrogen and β-tetrazolyl, or (7) keto;

or a pharmaceutically acceptable salt thereof; except compounds in which:

The A ring has a $C_3$–$C_4$ double bond, the B ring has a $C_5$–$C_6$ double double bond, $R^1$ is $CH_3$, and $R^3$ is keto;

The A ring has a $C_3$–$C_4$ double bond, the B ring has a $C_5$–$C_6$ double bond and the D ring has a $C_{16}$–$C_{17}$ double bond, $R^1$ is $CH_3$, and $R^3$ is $COOCH_3$; and The B ring has a $C_5$–$C_6$ double bond, $R^1$ is $CH_3$, and $R^3$ is $COCH_3$.

2. A compound of claim 1 having the following formula:

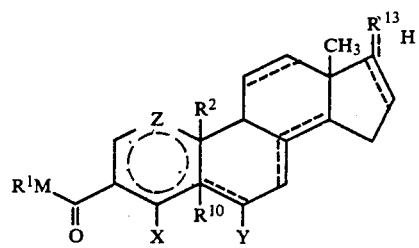 (II)

in which:

The A ring has up to 2 double bonds;

The B and C rings have optional double bonds where indicated by the broken lines, provided that the A-B rings do not have adjacent double bonds;

M is O or S;

X is H or halo, $R^1$ is H or $C_{1-8}$alkyl;

$R^2$ is absent or present as H or $CH_3$, provided $R^2$ is absent when the carbon to which it is attached is double bonded;

$R^{10}$ is absent when there is a $C_4$–$C_5$, $C_5$–$C_6$, or $C_5$–$C_{10}$ double bond, or present as an alpha hydrogen; and $R^{13}$ is (a) $CH(CH_3)CH_2OR^{20}$ wherein $R^{20}$ is H or $C_{1-6}$alkyl, or (b) $CONR^{21}R^{22}$ wherein $R^{21}$ and $R^{22}$ independently are H or $C_{1-8}$alkyl or a pharmaceutically acceptable salt thereof.

3. A compound of claim 2 wherein $R^2$ is methyl or a pharmaceutically acceptable salt thereof.

4. The compound of claim 3 that is 20-α-(hydroxymethyl)-5-α-pregn-3-ene-3-carboxylic acid or a pharmaceutically acceptable salt thereof.

5. The compound of claim 3 that is N,N-diisopropyl-5-α-androst-3-ene-17β-carboxamide-3-carboxylic acid or a pharmaceutically acceptable salt thereof.

6. The compound of claim 3 that is N,N-diisopropyl-androst-3,5-diene-17β-carboxamide-3-carboxylic acid or a pharmaceutically acceptable salt thereof.

7. The compound of claim 3 that is 17β-(N,N-diisopropylcarboxamide)-4-fluoro-5-α-androst-3-ene-3-carboxylic acid or a pharmaceutically acceptable salt thereof.

8. The compound of claim 3 that is 17β-(N,N-diisopropylcarboxamide)-4-fluoro-androst-3,5-diene-3-carboxylic acid or a pharmaceutically acceptable salt thereof.

9. The compound of claim 3 that is 20-α-(hydroxymethyl)-4-fluoro-5-α-pregn-3-ene-3-carboxylic acid or a pharmaceutically acceptable salt thereof.

10. The compound of claim 3 that is 3-carbomethoxy-N,N-diisopropyl-androst-3,5-diene-17β-carboxamide or a pharmaceutically acceptable salt thereof.

11. The compound of claim 3 that is 17β-N,N-diisopropylcarboxamide-5-α-androst-1,3-diene-3-carboxylic acid or a pharmaceutically acceptable salt thereof.

12. The compound of claim 3 that is N-t-butylandrost-3,5-diene-17β-carboxamide-3-carboxylic acid or a pharmaceutically acceptable salt thereof.

13. The compound of claim 3 that is N,N-diisopropyl-5-α-androst-2-ene-17β-carboxamide-3-carboxylic acid or a pharmaceutically acceptable salt thereof.

14. The compound of claim 3 that is N,N-diisopropyl-androst-2,4-diene-17β-carboxamide-3-carboxylic acid or a pharmaceutically acceptable salt thereof.

15. The compound of claim 3 that is N,N-diisopropyl-5-α-androstane-17β-carboxamide-3β-carboxylic acid or pharmaceutically acceptable salt thereof.

16. The compound of claim 2 that is N,N-diisopropyl-estr-3,5(10)-diene-17β-carboxamide-3-carboxylic acid or a pharmaceutically acceptable salt thereof.

17. The compound of claim 3 that is N,N-diisopropyl-estr-3,5-diene-17β-carboxamide-3-carboxylic acid or a pharmaceutically acceptable salt thereof.

18. The compound of claim 3 that is 17β-(N-t-butylcarboxamide)-androst-3,5,11-triene-3-carboxylic acid or 17β-(N-t-butylcarboxamide)-androst-3,5-diene-3-thiocarboxylic acid or a pharmaceutically acceptable salt thereof.

19. The compound of claim 2 that is
N-t-Butyl-5-α-androst-3-ene-17β-carboxamide-3-carboxylic acid;
17β-(N-t-Butylcarboxamide)-6-fluoro-5-α-androst-3-ene-3-carboxylic acid;
17β-(N-t-Butylcarboxamide)-6-fluoro-androst-3,5-diene-3-carboxylic acid;
3-Carbomethoxy-N-t-butyl-androst-3,5-diene-17β-carboxamide,
17β-N-t-Butylcarboxamide-5-α-androst-1,3-diene-3-carboxylic acid;
N-t-Butyl-5-α-androst-2-ene-17β-carboxamide-3-carboxylic acid;
N-t-Butyl-androst-2,4-diene-17β-carboxamide-3-carboxylic acid;
N-t-Butyl-5α-androstane-17β-carboxamide-3-carboxylic acid;
N-t-Butyl-estr-3,5(10)-diene-17β-carboxamide-3-carboxylic acid; or
N-t-Butyl-estr-3,5-diene-17β-carboxamide-3-carboxylic acid.

20. A pharmaceutical composition comprising a suitable pharmaceutical carrier and a compound of the formula:

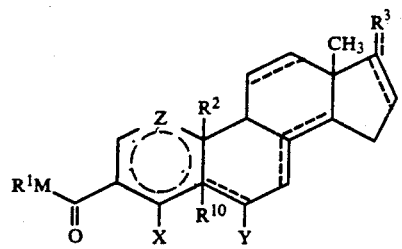

in which:

The A ring has up to 2 double bonds;
The B, C, and D rings have optional double bonds where indicated by the broken lines, provided the A-B rings and the B-C rings do not have adjacent double bonds and the D ring does not have a $C_{16}$–$C_{17}$ double bond when $R^3$ represents two substituents or a divalent substituent;

M is O or S;

Z is $CH_2$ or , when part of a double bond, CH;

X is H, Cl, F, Br, I, $CF_3$, or $C_{1-6}$ alkyl;

Y is H, $CF_3$, F, or Cl, $CH_3$, provided that Y is H when there is no $C_5$–$C_6$ double bond;

$R^1$ is H;

$R^2$ is absent or present as H or $CH_3$, provided $R^2$ is absent when the carbon to which it is attached is double bonded;

$R^{10}$ is absent when there is a $C_4$–$C_5$, $C_5$–$C_6$, or $C_5$–$C_{10}$ double bond, or present as an alpha hydrogen; and $R^3$ is
(1) α-hydrogen, α-hydroxyl, or α-acetoxy and/or
(a)

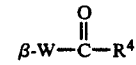

where W is a bond or $C_{1-12}$ alkyl
and $R^4$ is
(i) hydrogen,
(ii) hydroxyl,
(iii) $C_{18}$alkyl,
(iv) hydroxy $C_{1-8}$alkyl,
(v) $C_{1-8}$alkoxy,
(vi) NR $R^6$, where $R^5$ and $R^6$ are each independently selected from hydrogen, $C_{1-8}$-alkyl, $C_{3-6}$cycloalkyl, phenyl; or $R^5$ and $R^6$ taken together with the nitrogen to which they are attached represent a 5–6 membered saturated ring comprising up to one other heteroatom selected from oxygen and nitrogen, or
(vii) $OR^7$, where $R^7$ is hydrogen, alkali metal, $C_{1-18}$alkyl, benzyl, or
(b) β-Alk-$OR^8$, where Alk is $C_{1-12}$alkyl, and $R^8$ is
(i) phenyl$C_{1-6}$alkylcarbonyl,
(ii) $C_{5-10}$cycloalkylcarbonyl,
(iii) benzoyl,
(iv) $C_{1-8}$alkoxycarbonyl,
(v) aminocarbonyl, or $C_{1-8}$alkyl substituted aminocarbonyl,
(vi) hydrogen, or
(vii) $C_{1-8}$alkyl, (2) =CH—W—CO—$R^4$ or =CH—W-$OR^8$, where W is a bond or $C_{1-12}$alkyl, and $R^4$ and $R^8$ have the same meaning as above and $R^8$ also is hydrogen or $C_{1-20}$alkylcarbonyl;

(3)

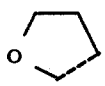

where the dashed bond replaces the 17-α-hydrogen, (4) α-hydrogen and β-NHCOR$^9$ where $R^9$ is $C_{1-12}$alkyl or β-NR$^5$R$^6$ where $R^5$ and $R^6$ have the same meaning as above, (5) α-hydrogen and β-cyano, (6) α-hydrogen and β-tetrazolyl, or (7) keto;

or a pharmaceutically acceptable salt thereof.

21. A composition of claim 20 wherein $R^2$ is methyl or a pharmaceutically acceptable salt thereof.

22. A composition of claim 20 wherein the compound is 20-α-(hydroxymethyl)-5-α-pregn-3-ene-3-carboxylic acid or a pharmaceutically acceptable salt thereof.

23. A composition of claim 20 wherein the compound is N,N-diisopropyl-5-α-androst-3-ene-17β-carboxamide-3-carboxylic acid or a pharmaceutically acceptable salt thereof.

24. A composition of claim 20 wherein the compound in N,N-diisopropyl-androst-3,5-diene-17β-carboxamide-3-carboxylic acid or a pharmaceutically acceptable salt thereof.

25. A composition of claim 20 wherein the compound is 17β-(N,N-diisopropylcarboxamide)-4-fluoro-5-α-androst-3-ene-3-carboxylic acid or a pharmaceutically acceptable salt thereof.

26. A composition of claim 20 wherein the compound is 20α-(hydroxymethyl)-4-fluoro-5-α-pregn-3-ene-3-carboxylic aicd or a pharmaceutically acceptable salt thereof.

27. A composition of claim 20 wherein the compound is 17β-N,N-diisopropylcarboxamide-5-α-androst-1,3-diene-3-carboxylic acid or a pharmaceutically accetpable salt thereof.

28. A composition of claim 20 wherein the compound is 17β-(N,N-diisopropylcarboxamide)-4-fluoroandrost-3,5-diene-3-carboxylic acid or a pharmaceutically acceptable salt thereof.

29. A composition of claim 20 wherein the compound is N-t-butyl-androst-3,5-diene-17β-carboxamide-3-carboxylic acid or a pharmaceutically acceptable salt thereof.

30. A composition of claim 20 wherein the compound is N,N-diisopropyl-5-α-androst-2-ene-17βcarboxamide-3-carboxylic acid or a pharmaceutically acceptable salt thereof.

31. A composition of claim 20 wherein the compound is N,N-diisopropyl-androst-2,4-diene-17β-carboxamide-3-carboxylic acid or a pharmaceutically acceptable salt thereof.

32. A composition of claim 20 wherein the compound is N,N-diisopropyl-5-α-androstane-17β-carboxamide-3β-carboxylic acid or a pharmaceutically acceptable salt thereof.

33. The composition of claim 20 wherein the compound is N,N-diisopropyl-estr-3,5(10)diene-17β-carboxamide-3-carboxylic acid or a pharmaceutically acceptable salt thereof.

34. The composition of claim 20 wherein the compound is N,N-diisopropyl-estr-3,5-diene-17β-carboxamide-3-carboxylic acid or a pharmaceutically acceptable salt thereof.

35. The composition of claim 20 wherein the compound is 17β-(N-t-butylcarboxamide)-androst-3,5,11-triene-3-carboxylic acid or 17β-(N-t-butylcarboxamide)-androst-3,5diene-3-thiocarboxylic acid or a pharmaceutically acceptable salt thereof.

36. The composition of claim 20 wherein the compound is:

N-t-Butyl-5-αandrost-3-ene-17β-carboxamide-3-carboxylic acid;

17β-(N-t-Butylcarboxamide)-6-fluoro-5-αandrost-3-ene-3-carboxylic acid;

17β-(N-t-Butylcarboxamide)-6-fluoro-androst-3,5-diene-3-carboxylic acid;

17β-N-t-Butylcarboxamide-5-α-androst-1,3-diene-3-carboxylic acid;

N-t-Butyl-5-αandrost-2-ene-17β-carboxamdie-3-carboxylic acid;

N-t-Butyl-androst-2,4-diene-17β-carboxamdie-3-carboxylic acid;

N-t-Butyl-5-α-androstane-17β-carboxamide-3-carboxylic acid;

N-t-Butyl-estr-3,5(10)-diene-17β-carboxamide-3-carboxylic acid; or

N-t-Butyl-estr-3,5-diene-17β-carboxamdie-3-carboxylic acid.

37. A method of inhibiting steroid 5-α-reductase activity in mammals that comprises administering to a subject an effective amount of a compound of the formula:

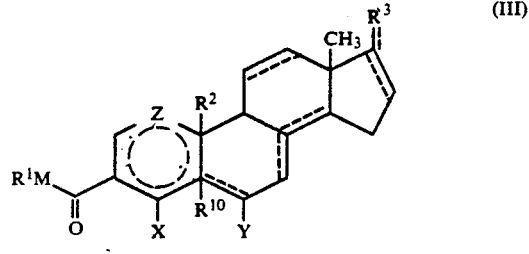

in which:

The A ring has up to 2 double bonds;

The B, C, and D rings have optional double bonds where indicated by the broken lines provided that the A-B rings and the B-C rings do not have adjacent double bonds and the D ring does not have a $C_{16}$–$C_{17}$ double bond when $R^3$ represents two substituents or a divalent substituent;

M is O or S;

Z is $CH_2$ or, when part of a double bond, CH;

X is H, Cl, F, Br, I, $CF_3$, or $C_{1-6}$alkyl;

Y is H, $CF_3$, F, or Cl, $CH_3$, provided that Y is H when there is no $C_5$–$C_6$ double bond;

$R^1$ is H or $C_{1-8}$alkyl;

$R^2$ is absent or present as H or $CH_3$, provided $R^2$ is absent when the carbon to which it is attached is double bonded;

$R^{10}$ is absent when there is a $C_4$–$C_5$, $C_5$–$C_6$, or $C_5$–$C_{10}$ double bond, or present as an alpha hydrogen; and $R^3$ is (1) α-hydrogen, α-hydroxyl, or α-acetoxy and/or (a)

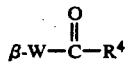

where W is a bond or $C_{1-12}$alkyl
and $R^4$ is
(i) hydrogen,
(ii) hydroxyl,
(iii) $C_{1-8}$alkyl,
(iv) hydroxy $C_{1-8}$alkyl,
(v) $C_{1-8}$alkoxy,
(vi) $NR^5R^6$, where $R^5$ and $R^6$ are each independently selected from hydrogen, $C_{1-8}$-alkyl, $C_{3-6}$cycloalkyl, phenyl; or $R^5$ and $R^6$ taken together with the nitrogen to which they are attached represent a 5-6 membered saturated ring comprising up to one other heteroatom selected from oxygen and nitrogen, or
(vii) $OR^7$, where $R^7$ is hydrogen, alkali metal, $C_{1-18}$alkyl, benzyl, or (b) $\beta$-Alk-$OR^8$, where Alk is $C_{1-12}$alkyl, and $R^8$ is
(i) phenyl $C_{1-6}$alkylcarbonyl,
(ii) $C_{5-10}$cycloalkylcarbonyl,
(iii) benzoyl,
(iv) $C_{1-8}$alkoxycarbonyl,
(v) aminocarbonyl, or $C_{1-8}$alkyl substituted aminocarbonyl,
(vi) hydrogen, or
(vii) $C_{1-8}$alkyl, (2) =CH—W—CO—$R^4$ or =CH—W—$OR^8$, where W is a bond or $C_{1-12}$alkyl, and $R^4$ and $R^8$ have the same meaning as above and $R^8$ also is hydrogen or $C_{1-20}$alkylcarbonyl;

(3)

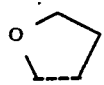

where the dashed bond replaces the 17α-hydrogen,
(4) α-hydrogen and β-$NHCOR^9$ where $R^9$ is $C_{1-12}$alkyl or β-$NR^5R^6$ where $R^5$ and $R^6$ have the same meaning as above,
(5) α-hydrogen and β-cyano,
(6) α-hydrogen and β-tetrazolyl, or
(7) keto; or
pharmaceutically acceptable salt thereof.

38. A method of claim 37 wherein $R^2$ is methyl or a pharmaceutically acceptable salt thereof.

39. A method of claim 37 wherein the compound is 20-α-(hydroxymethyl)-5-α-pregn-3-ene-3-carboxylic acid or a pharmaceutically acceptable salt thereof.

40. A method of claim 37 wherein the compound is N,N-diisopropyl-5-α-androst-3-ene-17β-carboxamide-3-carboxylic acid or a pharmaceutically acceptable salt thereof.

41. A method of claim 37 wherein the compound is N,N-diisopropyl-androst-3,5-diene-17β-carboxamide-3-carboxylic acid or a pharmaceutically acceptable salt thereof.

42. A method of claim 37 wherein the compound is 17β-(N,N-diisopropylcarboxamide)-4-fluoro-5-α-androst-3-ene-3-carboxylic acid or a pharmaceutically acceptable salt thereof.

43. A method of claim 37 wherein the compound is 20-α-(hydroxymethyl)-4-fluoro-5-α-pregn-3-ene-3-carboxylic acid or a pharmaceutically acceptable salt thereof.

44. A method of claim 37 wherein the compound is 17β-diisopropylcarboxamide-5-α-androst-1,3-diene-3-carboxylic acid or a pharmaceutically acceptable salt thereof.

45. A method of claim 37 wherein the compound is 17β-(N,N-diisopropylcarboxamide)-4-fluoro-androst-3,5-diene-3-carboxylic acid or a pharmaceutically acceptable salt thereof.

46. The method of claim 37 wherein the compound is N-t-butyl-androst-3,5-diene-17β-carboxamide-3-carboxylic acid or a pharmaceutically acceptable salt thereof.

47. The method of claim 37 wherein the compound is N,N-diisopropyl-5-α-androst-2-ene-17β-carboxamide-3-carboxylic acid or a pharmaceutically acceptable salt thereof.

48. The method of claim 37 wherein the compound is N,N-diisopropyl-androst-2,4-diene-17β-carboxamide-3-carboxylic acid or a pharmaceutically acceptable salt thereof.

49. The method of claim 37 wherein the compound is N,N-diisopropyl-5-α-androstane-17β-carboxamide-3β-carboxylic acid or a pharmaceutically acceptable salt thereof.

50. The method of claim 37 wherein the compound is N,N-diisopropyl-estr-3,5(10)-diene-17β-carboxamide-3-carboxylic acid or a pharmaceutically acceptable salt thereof.

51. The method of claim 37 wherein the compound is N,N-diisopropyl-estr-3,5-diene-17β-carboxamide-3-carboxylic acid or a pharmaceutically acceptable salt thereof.

52. The method of claim 37 wherein the compound is 17β-(N-t-butylcarboxamide)-androst-3,5,11-triene-3-carboxylic acid or 17β-(N-t-butylcarboxamide)-androst-3,5-diene-3-thiocarboxylic acid or a pharmaceutically acceptable salt thereof.

53. The method of claim 37 wherein the compound is:
N-t-Butyl-5-α-androst-3-ene-17β-carboxamide-3-carboxylic acid;
17β-(N-t-Butylcarboxamide)-6-fluoro-5-α-androst-3-ene-3-carboxylic acid;
17β-(N-t-Butylcarboxamide)-6-fluoro-androst-3,5-diene-3-carboxylic acid;
17β-N-t-Butylcarboxamide-5-α-androst-1,3-diene-3-carboxylic acid;
N-t-Butyl-5-α-androst-2-ene-17β-carboxamide-3-carboxylic acid;
N-t-Butyl-androst-2,4-diene-17β-carboxamide-3-carboxylic acid;
N-t-Butyl-5-α-androstane-17β-carboxamide-3-carboxylic acid;
N-t-Butyl-estr-3,5(10)-diene-17β-carboxamide-3-carboxylic acid; or
N-t-Butyl-estr-3,5-diene-17β-carboxamide-3-carboxylic acid.

54. A method of reducing or maintaining prostate size in a mammal that comprises administering to a subject an effective amount of a compound of the Formula:

(III)

in which:

The A ring has up to 2 double bonds;

The B, C, and D rings have optional double bonds where indicated by the broken lines, provided that the A-B rings and the B-C rings do not have adjacent double bonds and the D ring does not have a $C_{16}$–$C_{17}$ double bond when $R^3$ represents two substituents or a divalent substituent;

M is O or S;

Z is $CH_2$ or, when part of a double bond, CH;

X is H, Cl, Br, F, I, $CF_3$, or $C_{1-6}$alkyl;

Y is H, $CF_3$, F, or Cl, $CH_3$, provided that Y is H when there is no $C_5$–$C_6$ double bond;

$R^1$ is H;

$R^2$ is absent or present as H or $CH_3$, provided $R^2$ is absent when the carbon to which it is attached is double bonded;

$R^{10}$ is absent when there is a $C_4$–$C_5$, $C_5$–$C_6$, or $C_5$–$C_{10}$ double bond, or present as an alpha hydrogen; and $R^3$ is (1) α-hydrogen, α-hydroxyl, or acetoxy and/or (a)

$$\beta\text{-W}-\overset{\overset{\displaystyle O}{\|}}{C}-R^4$$

where W is a bond or $C_{1-12}$alkyl, an $R^4$ is
(i) hydrogen,
(ii) hydroxyl,
(iii) $C_{1-8}$alkyl,
(iv) hydroxy $C_{1-8}$alkyl,
(v) $C_{1-8}$alkoxy,
(vi) $NR^5R^6$, where $R^5$ and $R^6$ are each independently selected from hydrogen, $C_{1-8}$-alkyl, $C_{3-6}$cycloalkyl, phenyl; or $R^5$ and $R^6$ taken together with the nitrogen to which they are attached represent a 5–6 membered saturated ring comprising up to one other heteroatom selected from oxygen and nitrogen, or
(vii) $OR^7$, where $R^7$ is hydrogen, alkali metal, $C_{1-18}$alkyl, benzyl, or (b) β-Alk-$OR^8$, where Alk is $C_{1-12}$alkyl, and $R^8$ is
(i) phenyl $C_{1-6}$alkylcarbonyl,
(ii) $C_{5-10}$cycloalkylcarbonyl,
(iii) benzoyl,
(iv) $C_{1-8}$alkoxycarbonyl,
(v) aminocarbonyl, or $C_{1-8}$alkyl, substituted aminocarbonyl,
(vi) hydrogen, or
(vii) $C_{1-8}$alkyl, (2) =CH—Alk—CO—$R^4$ or =CH—Alk—$OR^8$, where Alk is present or absent, and $R^4$ and $R^8$ have the same meaning as above and $R^8$ also is hydrogen or $C_{1-20}$alkylcarbonyl;

(3)

where the dashed bond replaces the 17-α-hydrogen, (4) α-hydrogen and β-NHCOR$^9$ where $R^9$ is $C_{1-12}$alkyl or β-$NR^5R^6$ where $R^5$ and $R^6$ have the same meaning as above, (5) α-hydrogen and β-cyano, (6) α-hydrogen and β-tetrazolyl, or (7) keto;

or a pharmaceutically acceptable salt thereof.

55. A method of claim 54 wherein the compound is N-t-butyl-androst-3,5-diene-17β-carboxamide-3-carboxylic acid or N,N-diisopropyl-androst-3,5-diene-17β-carboxamide-3-carboxylic acid or a pharmaceutically acceptable salt thereof.

56. A compound of the formula:

(IV)

in which:

The A ring has up to 2 double bonds;

The B, C and D rings have optional double bonds where indicated by the broken lines, provided that the A-B rings and the B-C rings do not have adjacent double bonds and the D ring does not have a $C_{16}$–$C_{17}$ double bond when $R^{14}$ represents two substituents or a divalent substituent;

Z is $CH_2$ or, when part of a double bond, CH;

X is H, Cl, Br, F, I, $CF_3$, or $C_{1-6}$alkyl;

Y is H, $CF_3$, F, or Cl, $CH_3$, provided that Y is H when there is no $C_5$–$C_6$ double bond;

$R^2$ is absent or present as H or $CH_3$, provided $R^2$ is absent when the carbon to which it is attached is doubled bonded;

$R^{10}$ is absent when there is a $C_4$–$C_5$, $C_5$–$C_6$, or $C_5$–$C_{10}$ double bond, or present as an alpha hydrogen; and $R^{14}$ is (1) α-hydrogen, =-hydroxyl, or acetoxy and/or (a)

$$\beta\text{-W}-\overset{\overset{\displaystyle O}{\|}}{C}-R^4$$

where W is a bond or $C_{1-12}$alkyl, and $R^4$ is
(i) hydrogen,
(ii) hydroxyl,
(iii) $C_{1-8}$alkyl,
(iv) hydroxy $C_{1-8}$alkyl,
(v) $C_{1-8}$alkoxy,
(vi) $NR^5R^6$, where $R^5$ and $R^6$ are each independently selected from hydrogen, $C_{1-8}$-alkyl, $C_{3-6}$cycloalkyl, phenyl; or $R^5$ and $R^6$ taken together with the nitrogen to which they are attached represent a 5-6 membered saturated ring comprising up to one other heteroatom selected from oxygen ad nitrogen, or (vii) $OR^7$, where $R^7$ is hydrogen, alkali metal, $C_{1-18}$alkyl, benzyl, or (b) $\beta$-Alk-$OR^8$, where Alk is $C_{1-12}$alkyl, and $R^8$ is
(i) phenyl $C_{1-6}$alkylcarbonyl,
(ii) $C_{5-10}$cycloalkylcarbonyl,
(iii) benzoyl,
(iv) $C_{1-8}$alkoxycarbonyl,
(v) aminocarbonyl, or $C_{1-8}$alkyl substituted aminocarbonyl,
(vi) hydrogen, or
(vii) $C_{1-8}$alkyl, (2) =CH—Alk—CO—$R^4$ or =CH—Alk—$OR^8$, where Alk is present or absent, and $R^4$ and $R^8$ have the same meaning as above and $R^8$ also is hydrogen or $C_{1-20}$alkylcarbonyl;

(3)

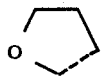

where the dashed bond replaces the 17-$\alpha$-hydrogen, (4) $\alpha$-hydrogen and $\beta$-NHCOR$^9$ where $R^9$ is $C_{1-12}$ alkyl or $\beta$-NR$^5$R$^6$ where $R^5$ and $R^6$ have the same meaning as above, (5) $\alpha$-hydrogen and $\beta$-cyano, (6) $\alpha$-hydrogen and $\beta$-tetrazolyl, or (7) keto;

or moieties which can be chemically converted to moieties (1) through (7);

except compounds in which:
the A ring has a $C_3$-$C_4$ double bond, and B ring has a $C_5$-$C_6$ double bond, and $R^{14}$ is keto; and the B ring has a $C_5$-$C_6$ double bond and $R^{14}$ is COCH$_3$.

57. The compound of claim 56 that is 20-$\alpha$-(t-butyldimethylsiloxymethyl)-3-(trifluoromethylsulfonate)-5-$\alpha$-pregn-3-ene, 17$\beta$-(t-butyldimethylsilyloxymethyl)-3-(trifluoromethylsulfonate)-5-$\alpha$-androst-3-ene, 17$\beta$-(N,N-diisopropylcarboxamide)-3-(trifluoromethylsulfonate)-androst-3,5-diene, 71$\beta$-(N,N-diisopropylcarboxamide)-3-(trifluoromethylsulfonate)-4-fluoro-5-$\alpha$-androst-1,3-diene, 20-$\alpha$-(t-butyldimethylsilyloxymethyl)-4-fluoro-3-(trifluoromethylsulfonate)-5-$\alpha$-pregn-1,3-diene, 17$\beta$-(N,N-diisopropylcarboxamide)-3-(trifluoromethylsulfonate)-5-$\alpha$-androst-1,3-diene, 17$\beta$-(N-t-butylcarboxamide)-3-(trifluoromethylsulfonate) androst-3,5-diene, 17$\beta$-(N,N-diisopropylcarboxamide)-3-(trifluoromethylsulfonate)-5$\alpha$-androst-2-ene, or 17$\beta$-(N,N-diisopropylcarboxamide)-3-(trifluoromethylsulfonate)-androst-2,4-diene.

58. A compound of the formula

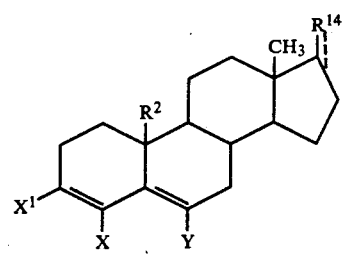

in which
$X^1$ is bromo, chloro, fluoro, or iodo;
$R^2$ is absent or present as H or CH$_3$;
X is H, Cl, F, Br, I, CF$_3$, or $C_{1-6}$alkyl;
Y is H, CF$_3$, F, or Cl, CH$_3$, provided that Y is H when there is no $C_5$-$C_6$ double bond; and
$R^{14}$ is
(1) $\alpha$-hydrogen, $\alpha$-hydroxyl, or acetoxy and/or
(a)

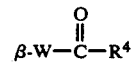

where W is a bond or
$C_{1-12}$alkyl, and $R^4$ is
(i) hydrogen,
(ii) hydroxyl,
(iii) $C_{1-8}$alkyl,
(iv) hydroxy $C_{1-8}$alkyl,
(v) $C_{1-8}$alkoxy,
(vi) NR$^5$R$^6$, where $R^5$ and $R^6$ are each independently selected from hydrogen, $C_{1-8}$-alkyl, $C_{3-6}$cycloalkyl, phenyl; or $R^5$ and $R^6$ taken together with the nitrogen to which they are attached represent a 5-6 membered saturated ring comprising up to one other heteroatom selected from oxygen and nitrogen, or
(vii) $OR^7$, where $R^7$ is hydrogen, alkali metal, $C_{1-18}$alkyl, benzyl, or (b) $\beta$-Alk-$OR^8$, where Alk is $C_{1-12}$alkyl, and $R^8$ is
(i) phenyl$C_{1-6}$alkylcarbonyl,
(ii) $C_{5-10}$cycloalkylcarbonyl,
(iii) benzoyl,
(iv) $C_{1-8}$alkoxycarbonyl,
(v) aminocarbonyl or $C_{1-8}$alkyl substituted aminocarbonyl,
(vi) hydrogen, or
(vii) $C_{1-8}$alkyl, (2) =CH—Alk—CO—$R^4$ or =CH—Alk—$OR^8$, where Alk is present or absent, and $R^4$ and $R^8$ have the same meaning as above and $R^8$ also is hydrogen or $C_{1-20}$alkylcarbonyl;

(3)

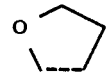

where the dashed bond replaces the 17-$\alpha$-hydrogen, (4) $\alpha$-hydrogen and $\beta$-NHCOR$^9$ where $R^9$ is $C_{1-12}$ alkyl or $\beta$-NR$^5$R$^6$ where $R^5$ and $R^6$ have the same meaning as above, (5) $\alpha$-hydrogen and $\beta$-cyano, (6) α-hydrogen and β-tetrazolyl, or
(7) keto;
or moieties which can be chemically converted to moieties (1) through (7);
except compounds in which:
$X^1$ is Cl and $R^{14}$ is β-CH$_3$CO;
$X^1$ is Cl and $R^{14}$ is β-OH and α-CH$_3$CO$_2$;
and
$X^1$ is Br and $R^{14}$ is β-OH and α-CH$_3$CO$_2$.

59. A compound of claim 58 wherein $X^1$ is bromo.

60. A compound of claim 59 that is N-t-Butyl androst-3,5-diene-3-bromo-17β-carboxamide or N,N-diisopropyl-androst-3,5-diene-3-bromo-17β-carboxamide.

61. A process for preparing compounds of the formula:

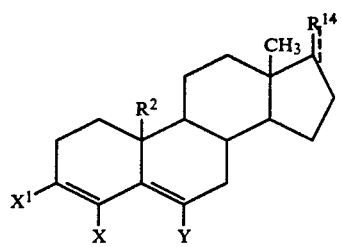

(VII)

in which
$X^1$ is bromo, chloro, or iodo;
$R^2$ is absent or present as H or CH$_3$,
X is H, Cl, F, Br, I, CF$_3$, or C$_{1-6}$alkyl;
Y is H, CF$_3$, F, or Cl, CH$_3$, provided that Y is H when there is no C$_5$–C$_6$ double bond; and
$R^{14}$ is
(1) α-hydrogen, α-hydroxyl, or acetoxy and/or
(a)

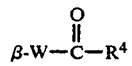

where W is a bond or C$_{1-12}$alkyl, and $R^4$ is
(i) hydrogen,
(ii) hydroxyl,
(iii) C$_{1-8}$alkyl,
(iv) hydroxy C$_{1-8}$alkyl,
(v) C$_{1-8}$alkoxy,
(vi) NR$^5$R$^6$, where R$^5$ and R$^6$ are each independently selected from hydrogen, C$_{1-8}$-alkyl, C$_{3-6}$-cycloalkyl, phenyl; or R$^5$ and R$^6$ taken together with the nitrogen to which they are attached represent a 5-6 membered saturated ring comprising up to one other heteroatom selected from oxygen and nitrogen, or
(vii) OR$^7$, where R$^7$ is hydrogen, alkali metal, C$_{1-18}$alkyl, benzyl, or
(b) β-Alk-OR$^8$, where Alk is C$_{1-12}$alkyl, and R$^8$ is
(i) phenyl C$_{1-6}$alkylcarbonyl,
(ii) C$_{5-10}$cycloalkylcarbonyl,
(iii) benzoyl,
(iv) C$_{1-8}$alkoxycarbonyl,
(v) aminocarbonyl, or C$_{1-8}$alkyl substituted aminocarbonyl,
(vi) hydrogen, or
(vii) C$_{1-8}$alkyl,
(2) =CH—Alk—CO—R$^4$ or =CH—Alk—OR$^8$, where Alk is present or absent, and R$^4$ and R$^8$ have the same meaning as above and $R^8$ also is hydrogen or C$_{1-20}$alkylcarbonyl;

(3)

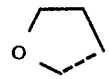

where the dashed bond replaces the 17-α-hydrogen,
(4) α-hydrogen and β-NHCOR$^9$ where R$^9$ is C$_{1-12}$alkyl or β-NR$^5$R$^6$ where R$^5$ and R$^6$ have the same meaning as above,
(5) α-hydrogen and β-cyano,
(6) α-hydrogen and β-tetrazolyl, or
(7) keto or moieties which can be chemically converted to moieties (1) through (7);
that comprises treating with a carboxylic acid halide or phosphorous polyhalide a compound of the formula:

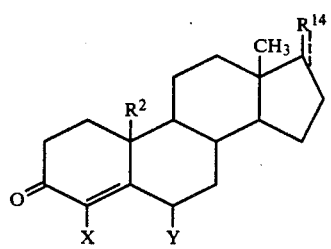

(VIII)

in which $R^2$, $R^{14}$, X and Y are as defined above, provided that X and Y do not include any such moities that render inoperative the above process;
except compounds in which:
$R^2$ is CH$_3$ and $R^{14}$ is keto; and
$R^2$ is CH$_3$ and $R^{14}$ is β-OH and α-CH$_3$CO$_2$.

62. The process of claim 61 wherein the compound prepared is N-t-butyl-androst-3,5-diene-3-bromo-17β-carboxamide or N,N-diisopropyl-androst-3,5-diene-3-bromo-17β-carboxamide.

63. The process of claim 61 further comprising the step of treating the compound prepared with an alkyl lithium reagent followed by a carboxylating agent, or with a palladium catalyst in presence of base, a C$_{1-4}$alkanol, and carbon monoxide to yield a compound of the formula:

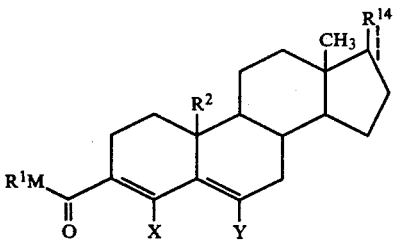

(IX)

in which
$R^2$, $R^{14}$, X and Y are as defined in claim 61,
$R^1$ is H or C$_{1-8}$alkyl; and
M is O or S.

64. The process of claim 63 wherein the compound prepared is N-t-butyl-androst-3,5-diene-17β-carboxamide-3-carboxylic acid or N,N-diisopropyl-androst-3,5-diene-17β-carboxamide-3-carboxylic acid.

65. A compound of claim 12 that is N-t-butyl-androst-3,5-diene-17β-carboxamide-3-carboxylic acid.

66. A compound of claim 12 that is N-t-butyl-androst-3,5-diene-17β-carboxamide-3-carboxylic acid sodium salt.

67. A composition of claim 29 wherein the compound is N-t-butyl-androst-3,5-diene-17β-carboxamide-3-carboxylic acid.

68. A method of claim 46 wherein the compound is N-t-butyl-androst-3,5-diene-17β-carboxyamide carboxylic acid.

* * * * *